United States Patent [19]

Parton et al.

[11] Patent Number: 4,471,044
[45] Date of Patent: Sep. 11, 1984

[54] SILVER HALIDE EMULSIONS AND PHOTOGRAPHIC ELEMENTS CONTAINING ADSORBABLE ALKYNYL SUBSTITUTED HETEROCYCLIC QUATERNARY AMMONIUM SALTS

[75] Inventors: Richard L. Parton; Wilbur S. Gaugh, both of Webster; Karl E. Wiegers, Rochester, all of N.Y.

[73] Assignee: Eastman Kodak Company, Rochester, N.Y.

[21] Appl. No.: 503,470

[22] Filed: Jun. 13, 1983

[51] Int. Cl.$^3$ .................. G03C 5/54; G03C 7/00; G03C 1/08; G03C 1/485
[52] U.S. Cl. .................................. 430/217; 430/598; 430/600; 430/611
[58] Field of Search ............... 430/217, 598, 600, 611, 430/613, 614

[56] References Cited

U.S. PATENT DOCUMENTS

| | | | |
|---|---|---|---|
| 3,255,013 | 6/1966 | Dersch | 430/602 |
| 3,615,615 | 10/1971 | Lincoln et al. | 430/598 |
| 3,719,494 | 3/1973 | Kurtz et al. | 430/598 |
| 3,734,738 | 5/1973 | Kurtz et al. | 430/598 |
| 3,854,956 | 12/1974 | Lincoln et al. | 260/240 |
| 4,030,925 | 6/1977 | Leone et al. | 430/598 |
| 4,031,127 | 6/1977 | Leone et al. | 260/552 R |
| 4,115,122 | 9/1978 | Adachi et al. | 430/598 |
| 4,243,739 | 1/1981 | Mifune et al. | 430/600 |
| 4,245,037 | 1/1981 | Tsujino | 430/598 |
| 4,276,364 | 6/1981 | Leone | 430/598 |
| 4,306,016 | 12/1981 | Baralle et al. | 430/598 |

OTHER PUBLICATIONS

Research Disclosure, Vol. 151, Nov. 1976, Item 15162.
Research Disclosure, Vol. 176, Dec. 1978, Item 17626.

*Primary Examiner*—Richard L. Schilling
*Attorney, Agent, or Firm*—Carl O. Thomas

[57] ABSTRACT

The use of thioamido and alkynyl substituted heterocyclic ammonium salts in producing images in silver halide photographic elements is disclosed. The thioamido and alkynyl substituted heterocyclic ammonium salts can be incorporated in photographic silver halide emulsions. The thioamido substituent is capable of promoting adsorption of these salts to silver halide grain surfaces. In negative working surface latent image forming emulsions the thioamido and alkynyl substituted heterocyclic ammonium salts permit higher speeds to be achieved. In direct positive internal latent image forming emulsions nucleation activity and improved incubation stability can be achieved.

36 Claims, No Drawings

4,471,044

SILVER HALIDE EMULSIONS AND PHOTOGRAPHIC ELEMENTS CONTAINING ADSORBABLE ALKYNYL SUBSTITUTED HETEROCYCLIC QUATERNARY AMMONIUM SALTS

FIELD OF THE INVENTION

This invention is directed to novel adsorbable alkynyl substituted quaternary ammonium salts and to silver halide emulsions and photographic elements in which they are incorporated. The invention is applicable to negative working surface latent image forming silver halide emulsions and to direct positive silver halide emulsions which form internal latent images.

BACKGROUND OF THE INVENTION

Hydrazines find a variety of uses in silver halide photography. They have been used in negative working surface latent image forming silver halide emulsions to increase speed and/or contrast. They have been used in direct positive internal latent image forming emulsions as nucleating agents. When incorporated in photographic elements as opposed to processing solutions hydrazines are frequently substituted with a group for reducing their mobility, such as a ballasting moiety or a moiety for promoting adsorption to silver halide grain surfaces. In one commonly employed form hydrazines take the form of arylhydrazides which contain a substituent for promoting adsorption to silver halide grain surfaces. Arylhydrazides containing adsorption promoting moieties are illustrated by Leone et al U.S. Pat. Nos. 4,030,925 and 4,031,127, Tsujino et al U.S. Pat. No. 4,245,037, Mifune et al U.S. Pat. No. 4,243,739, Leone U.S. Pat. No. 4,276,364, Research Disclosure, Vol. 151, November 1976, Item 15162 (note reduction sensitization, page 77, left column), and Sidhu et al Research Disclosure, Vol. 176, December 1978, Item 17626. Research Disclosure and Product Licensing Index are publications of Industrial Opportunities Ltd.; Homewell, Havant; Hampshire, P09 1EF, United Kingdom.

It has been suggested from time to time to employ heterocyclic quaternary ammonium salts as nucleating agents in direct positive emulsions. Heterocyclic quaternary ammonium salts employed for this purpose are illustrated by Lincoln et al U.S. Pat. Nos. 3,615,615 and 3,854,956, Kurtz et al U.S. Pat. Nos. 3,719,494 and 3,734,738, and Baralle et al U.S. Pat. No. 4,306,016.

Adachi et al U.S. Pat. No. 4,115,122 discloses heterocyclic quaternary ammonium salt compounds which are propargyl or butynyl substituted. Such compounds are disclosed to be among those satisfying the following structure:

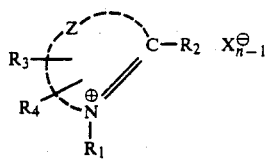

wherein

Z represents an atomic group necessary for forming a 5- or 6-membered heterocyclic nucleus, $R_1$ represents an aliphatic group, $R_2$ represents a hydrogen atom or an aliphatic group, $R_3$ and $R_4$, which may be the same or different, each represents a hydrogen atom, a halogen atom, an aliphatic group, an alkoxy group, a hydroxy group, or an aromatic group, at least one of $R_1$, $R_2$, $R_3$ and $R_4$ represents a propargyl group, a butynyl group, or a substituent containing a propargyl or butynyl group, $X^\ominus$ represents an anion, and n is 1 or 2, with n being 1 in the case that the compound forms an inner salt.

Some of the compounds satisfying formula I have been found to be highly effective nucleating agents in direct positive emulsions.

Dersch U.S. Pat. No. 3,255,013 discloses that condensation products of an alkylene oxide and 1,4-di-isobutyl-1,4-dimethylbutynediol are capable of producing speed increases similarly as alkylene oxide sensitizers, but do not require the special antifoggants usually employed in combination with alkylene oxide polymers and their condensation products.

SUMMARY OF THE INVENTION

This invention is directed to a photographically useful heterocyclic quaternary ammonium salt capable of being adsorbed to the surfaces of radiation sensitive siler halide grains of the formula:

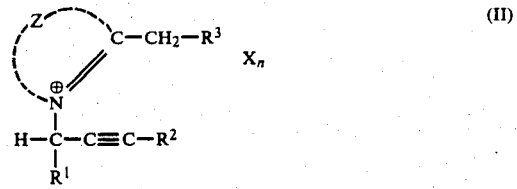

wherein

Z represents the atoms completing a hetrocyclic quaternary ammonium nucleus comprised of an azolium or azinium ring;

$R^1$ is hydrogen or methyl;

$R^2$ is hydrogen or an alkyl substituent of from 1 to 8 carbon atoms;

$R^3$ is hydrogen or a substituent having a Hammett sigma value derived electron withdrawing characteristic more positive than $-0.2$;

X is a charge balancing counter ion; and n is 0 or 1; and

Z or $R^3$ includes a thioamido adsorption promoting moiety.

The invention is also directed to radiation sensitive silver halide emulsions containing these heterocyclic quaternary ammonium salts adsorbed to silver halide grain surfaces and to photographic elements containing these emulsions.

It has been observed that the presence of the thioamido adsorption promoting moiety imparts unexpected incubation stability to direct positive emulsions in which the alkynyl substituted heterocyclic quaternary ammonium salt has been introduced as a nucleating agent. In addition the presence of the adsorption moiety allows comparable levels of nucleating activity to be achieved at lower concentration levels. When employed with negative working surface latent image forming silver halide emulsions, the presence of the thioamido adsorption promoting moiety in the alkynyl substituted heterocyclic quaternary ammonium salts of this invention allows these salts to increase photographic speed.

DESCRIPTION OF PREFERRED EMBODIMENTS

The present invention is directed to compounds which satisfy formula II above and their applications to silver halide photography. These compounds are surprisingly active in silver halide emulsions while structurally similar compounds show essentially no activity. Without being bound to any particular theory to account for the activity of the compounds of formula II while similar compounds fail to show activity, it is believed that the activity of compounds of formula II is attributable to their ability to effect ring closure to the interim form of formula III as shown below while similar, but inactive compounds investigated lack the proper substituent configuration for similar ring closure.

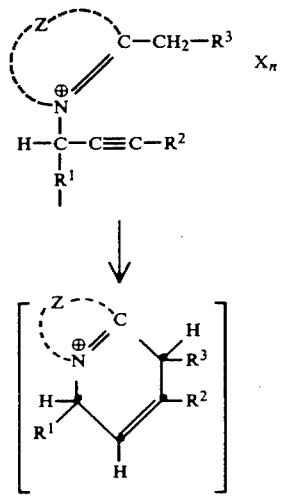

From formulae II and III it can be seen that $R^1$, $R^2$, and $R^3$ are groups which are neither altered nor displaced by ring closure. $R^1$ and $R^2$ are preferably each independently selected from hydrogen or methyl. While hydrogen and alkyl of from 1 to 8 carbon atoms is specifically contemplated for $R^2$, other $R^1$ substituents, though possible, have been generally observed to reduce activity. Considering $R^1$ and $R^2$ together, it is appreciated that the quaternized nitrogen atom is preferably substituted with alkynyl groups chosen from among 1-(2-propynyl), 1-(2-butynyl), 2-(3-butynyl), and 2-(3-pentynyl).

The methylene group to which $R^3$ is attached is activated by the azolium or azinium ring, which is a strong electron withdrawing group. $R^3$ is preferably hydrogen, thereby forming a methyl substituent of the azolium or azinium ring, but $R^3$ can also be any substituent which is compatible with retaining the methylene group in its activated condition. An activated methylene group is one in which at least one of the hydrogen atoms is rendered more readily displaceable. This facilitates ring closure and is believed to account for the photographic activity of the compounds of this invention.

Since the azolium and azinium nuclei are highly electron withdrawing, it is not essential that $R^3$ be electron withdrawing, although this is preferred. However, strongly electron donating substituents are not preferred. Published Hammett sigma values provide a convenient reference for selecting preferred substituents to satisfy $R^3$. In general $R^3$ is contemplated to embrace substituents having a Hammett sigma value derived electron withdrawing characteristic more positive than $-0.2$, preferably more positive than $-0.1$, where, for purposes of this invention meta position Hammett sigma values are chosen for identifying the Hammett sigma value derived electron withdrawing characteristics of individual substituents. A positive Hammett sigma value is indicative of an substituent which is capable of rendering a phenyl ring electron withdrawing while a negative Hammett sigma value is indicative of a substituent which is capable of rendering a phenyl ring electron donating. Hydrogen is assigned a Hammett sigma value of 0. Lange's Handbook of Chemistry, 12th Ed., McGraw-Hill, 1979, Table 3-12, pp. 3-135 to 3-138, lists Hammett sigma values for a large number of commonly encountered substituents. While the representative published Hammett sigma values listed below are capable of guiding substituent selection, variances in the degree of electron withdrawing or donating characteristics in the compounds of this invention are to be expected.

$R^3$ can in one form be a highly electron withdrawing substituent, such as a substituent having a Hammett sigma value derived electron withdrawing characteristic more positive than $+0.30$. Illustrative of such substituents are cyano ($\sigma = +0.61$), alkylcarbonyl substituents (e.g., acetyl $\sigma = +0.38$ and trifluoroacetyl $\sigma = +0.65$), arylcarbonyl substituents (e.g., phenylcarbonyl $\sigma = +0.34$), oxycarbonyl substituents, including alkoxycarbonyl and aryloxycarbonyl substituents (e.g., methoxycarbonyl $\sigma = +\mathbf{0.32}$, ethoxycarbonyl $\sigma = +0.37$), nitro ($\sigma = +0.71$), thiocyanato ($\sigma = +0.63$), perhaloalkyl substituents (e.g., trichloromethyl $\sigma = +0.47$ and trifluoromethyl $\sigma = +0.47$), perfluoroalkylthio substituents (e.g., trifluoromethylthio $\sigma = +0.35$), sulfamoyl substituents, including alkylsulfamoyl and arylsulfamoyl substituents (e.g., sulfamoyl $\sigma = +0.46$), carbonylthio substituents (e.g., acetylthio $\sigma = +0.39$), carbamoylthio substituents (e.g., carbamoylthio $\sigma = +0.34$), oxythio substituents, including alkoxythio and aryloxythio substituents (e.g., methoxythio $\sigma = +0.52$), and sulfonyl substituents, including alkylsulfonyl and arylsulfonyl substituents (e.g., methylsulfonyl $\sigma = +0.68$ and phenylsulfonyl $\sigma = +0.67$).

In addition to the highly electron withdrawing substituents identified above $R^3$ can be chosen from among a variety of substituents having Hammett sigma value derived electron withdrawing characteristics more positive than $-0.20$. Exemplary simple substituents from which $R^3$ can be selected and their published meta Hammett sigma values include primary and second alkyl substituents, such as methyl $\sigma = -0.07$, ethyl $\sigma = -0.07$, n-propyl $\sigma = -0.05$, i-propyl $\sigma = -0.07$, n-butyl $\sigma = -0.07$, and sec-butyl $\sigma = -0.07$. These alkyl substituents are synthetically convenient and therefore contemplated, though electron donating. Alkyl substituents containing tertiary carbon atoms and particularly tertiary alkyl groups tend to be even more highly electron donating and are not preferred. Aryl groups such as phenyl, α-naphthyl, and β-naphthyl groups are contemplated (e.g., phenyl $\sigma = +0.06$). Other useful and specifically contemplated hydrocarbon substituents include alkaryl substituents (e.g., p-methylphenyl), aralkyl substituents (e.g., benzyl $\sigma = -0.05$ and phenethyl), alkenyl substituents (e.g. vinyl $\sigma = +0.02$), aralkenyl substituents (e.g., 2-phenylvinyl $\sigma=+0.14$), alkynyl substituents (e.g., ethynyl $\sigma=+0.21$, propargyl, and 2-butynyl), and aralkynyl substituents (e.g., phenethynyl $\sigma=+0.14$). Substituted hydrocarbon substituents are also contemplated, such as haloalkyl substituents (e.g., bromomethyl, chloromethyl $\sigma=-0.12$, fluoromethyl, and iodomethyl), haloaryl substituents (e.g., p-bromphenyl, m-bromophenyl, and p-chlorophenyl), and hydroxyalkyl substituents (e.g., hydroxymethyl $\sigma=+0.08$). Oxy substituents or substituent moieties of hydrocarbon substituents are specifically contemplated—i.e., hydroxy ($\sigma=+0.10$), alkoxy (e.g., methoxy $\sigma=+0.14$, ethoxy $\sigma=+0.07$, n-propoxy $\sigma=+0.07$, i-propoxy $\sigma=0.00$, n-butoxy $\sigma=-0.05$, cyclohexoxy $\sigma=+0.29$, cyclohexylmethoxy $\sigma=+0.18$, and trifluoromethoxy $\sigma=+0.36$), and aryloxy (e.g., phenoxy $\sigma=+0.25$). Halogen substituents are contemplated—i.e., bromo ($\sigma=+0.39$), chloro ($\sigma=+0.35$), fluoro ($\sigma=+0.34$), and iodo ($\sigma=+0.35$). Amido substituents are also contemplated, such as amido ($\sigma=+0.25$), methylamido ($\sigma=+0.21$), phenylamido ($\sigma=+0.22$), and ureido ($\sigma=+0.18$).

Other synthetically convenient substituents which are not highly electron donating can alternatively be employed. In addition to the illustrative simple substituents identified above it is appreciated that larger substituents can be employed. Such substituents can, for instance, be comprised of combinations of moieties corresponding to the simple substituents described above. For example, larger substituents can correspond to conventional incorporated photographic addenda ballasting groups, such as ballasting groups of dye image forming couplers. Ballasting groups typically have from about 8 to 30 or more carbon atoms. Since the adsorption promoting moiety, described below, is primarily relied upon to locate the heterocyclic quaternary ammonium salts on silver halide grain surfaces, $R^3$ preferably contains 18 or fewer carbon atoms and most preferably 8 or fewer carbon atoms.

Z represents the atoms completing a heterocyclic quaternary ammonium nucleus comprising a 5 or 6 membered heterocyclic nucleus—i.e., an azolium or azinium nucleus. In general the hetrocyclic quaternary ammonium nucleus can be similar to heterocyclic quaternary ammonium nuclei found in cyanine dyes. Such nuclei can include optionally carbocyclic rings either pendant from or fused with the heterocyclic ring, and ring substituents. Quinolinium nuclei constitute specifically preferred heterocyclic quaternary ammonium nuclei. Benzothiazolium nuclei are also preferred. Other illustrative nuclei include pyridinium, thiazolinium, thiazolium, benzothiazolium, naphthothiazolium, selenazolium, benzoselenazolium, benzimidazolium, tetrazolium, and indolenium nuclei. Oxazolium and naphthoxazolium nuclei can be employed, though not preferred, while relatively poor performance has been observed with benzoxazolium nuclei.

Specific preferred examples of the above nuclei are (1) thiazolinium nuclei, such as 2-methyl-2-thiazolinium, 2-p-hydroxyphenyl-5-methyl-2-thiazolinium, 2-phenyl-2-thiazolinium, 2-ethyl-2-thiazolinium, 2-propyl-2-thiazolinium, and 2-thiazolinium nuclei; (2) thiazolium nuclei, such as thiazolium, 4-methylthiazolium, 4-phenylthiazolium, 4-(p-hydroxyphenyl)thiazolium, 5-methylthiazolium, 5-phenylthiazolium, 4,5-dimethylthiazolium, and 4,5-diphenylthiazolium nuclei; (3) benzothiazolium nuclei, such as benzothiazolium, 5-hydroxybenzothiazolium, 5-fluorobenzothiazolium, 5-chlorobenzothiazolium, 6-chlorobenzothiazolium, 5-methylbenzothiazolium, 6-methylbenzothiazolium, 5,6-dimethylbenzothiazolium, 5-bromobenzothiazolium, 5-hexylbenzothiazolium, 6-phenylbenzothiazolium, 5-methoxybenzothiazolium, 6-methoxybenzothiazolium, 5-iodobenzothiazolium, 5-ethoxybenzothiazolium, tetrahydrobenzothiazolium, 5,6-dimethoxybenzothiazolium, 5-hydroxybenzothiazolium, and 6-hydroxybenzothiazolium nuclei; (4) naphthothiazolium nuclei, such as α-naphthothiazolium, β-napthothiazolium, β,β-naphtothiazolium, 5-methoxy-β-naphthothiazolium, 5-ethoxy-β-naphthothiazolium, 7-methoxy-α-naphthothiazolium, 5-hydroxy-β-naphthothiazolium, 7-hydroxy-α-naphthothiazolium, and 5-ethyl-β-naphthothiazolium; (5) selenazolium nuclei, such as selenazolium, 4-methylselenazolium, and 4-phenylselenazolium nuclei; (6) benzoselenazolium nuclei, such as benzoselenazolium, 6-chlorobenzoselenazolium, 5-methoxybenzoselenazolium, 6-hydroxybenzoselenazolium, and tetrahydrobenzoselenazolium nuclei; (7) naphthoselenazolium nuclei, such as α-naphthoselenazolium, β-naphthoselenazolium, and β,β-naphthoselenazolium nuclei; (8) benzimidazolium nuclei, such as benzimidazolium, 1-ethylbenzimidazolium, 1-ethyl-5-chlorobenzimidazolium, 1-ethyl-5,6-dichlorobenzimidazolium, and 1-phenyl-5,6-dichlorobenzimidazolium nuclei; (9) tetrazolium nuclei, such as tetrazolium, 1-phenyltetrazolium, 2-phenyltetrazolium, 5-bromotetrazolium, 1,5-dimethyltetrazolium, 1-carboethoxytetrazolium, and 1-methyl-5-phenyltetrazolium nuclei; (10) pyridinium nuclei, such as pryidinium, 3-ethylpyridinium, 4-decylpyridinium, 4-benzylpyridinium, 4-phenylpyridinium, 4-chloropyridinium, 4-bromopyridinium, 4,6-dichloropyridinium, 6-bromopyridinium, 4-methoxypyridinium, 4-ethoxypyridinium, and 6-methoxypyridinium nuclei; (11) quinolinium nuclei, such as quinolinium, 3-methylquinolinium, 6-methylquinolinium, 8-methylquinolinium, 6-chloroquinolinium, 8-chloroquinolinium, 8-fluoroquinolinium, 6-methoxyquinolinium, 6-ethoxyquinolinium, 6-hydroxyquinolinium, and 8-hydroxyquinolinium nuclei; and (12) indolenium nuclei, such as indolenium, 3,3-dimethylindolenium, 5-hydroxy-3,3-dimethylindolenium, and 3,3-dimethyl-6-chloroindolenium nuclei.

$X_n$ is included in formulae II and III to indicate the presence of any counter ion required to render the heterocyclic quaternary ammonium salt ionically neutral. The charge balancing counter ion X can take the form of any anion known to be useful in offsetting the positive charge imparted to the salt by the quaternized nitrogen atom in the heterocyclic ring. For example, the anion can take the form of an acid anion, such as a tosylate, sulfate, halide, or similar anion commonly present in silver halide emulsion. In this case n is 1. When the salt also contains an anionic substituent, such as a sulfoalkyl substituent, the salt can take the form of a betaine, thereby eliminating the need for any counter ion. Where more than one anionic substituent is present in the salt, such as two sulfoalkyl substituents, a cationic counter ion, such as hydrogen ion or an alkali metal ion, can be present.

An important and distinguishing feature of the alkynyl substituted heterocyclic quaternary ammonium salts of this invention is the presence of a thioamido adsorption promoting moiety. While any linkage of the thioamido moiety which does not interfere with ring closure as shown in formula III is not precluded, it is preferred that the thioamido adsorption promoting moiety be linked through $R^3$ or, most preferably, that the thioamido adsorption promoting moiety be linked through the azolium or azinium nucleus Z.

The thioamido adsorption promoting moiety is characterized by containing a divalent thioamido group, such as indicated by formula IV:

$$\overset{S}{\underset{\|}{-C}}-\text{Amino-}. \qquad (IV)$$

The thioamido group can be part of a ring structure appended directly or indirectly to the azolium or azinium nucleus or to $R^3$. Alternatively and preferably the thioamido group can be an acyclic thioamido group, herein defined as requiring that the thiocarbonyl, —C(S)—, and Amino groups not be part of a ring structure. Useful thioamido adsorption promoting groups can be selected from among conventional thioamido adsorption promoting groups, such as those disclosed in Leone et al U.S. Pat. Nos. 4,030,925, 4,031,127, and 4,080,207, Tsujino et al U.S. Pat. No. 4,245,037, Hirano et al U.S. Pat. No. 4,255,511, Adachi et al U.S. Pat. No. 4,266,013, Leone U.S. Pat. No. 4,276,364, *Research Disclosure*, Item 15162, and Sidhu et al *Research Disclosure*, Item 17626, cited above.

Specifically preferred thioamido moieties can be presented by the following formula:

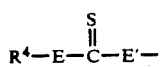

$$R^4-E-\overset{S}{\underset{\|}{C}}-E'- \qquad (V)$$

where one of E and E' represents —N($R^5$)— and the other represents —O—, —S—, or —N($R^6$)—, $R^4$ represents hydrogen, an aliphatic residue, an aromatic residue, or together with E or E' completes a 5 or 6 membered heterocyclic ring, $R^5$ or $R^6$ in the E position represents hydrogen, an aliphatic residue, or an aromatic residue, and $R^5$ and $R^6$ in the E' position represents hydrogen or a benzyl substituent when E' is bonded directly to an aromatic ring (e.g., Z or Ar, described below) and can otherwise be chosen from among the same substituents as when in the E position, provided that at least one of $R^4$, $R^5$, and $R^6$ must be hydrogen when each is present.

$R^5$ or $R^6$ in the E' position is preferably hydrogen. When $R^5$ and $R^6$ is a benzyl substituent, the ring can be unsubstituted or substituted, such as with alkyl, alkoxy, or halo groups. The alkyl moieties preferably contain from 1 to 8 carbon atoms. When E' is not linked directly to an aryl group—e.g., Z, $R^5$ and $R^6$ in the E' position can be chosen from among the same substituents as when in the E position.

When E and E' are both amino substituents, the entire adsorption promoting moiety is a thiourea group. In addition to hydrogen specifically preferred $R^4$ and $R^5$ or $R^6$ in the E position substituents include alkyl substituents such as alkoxyalkyl, haloalkyl (including perhaloalkyl—e.g., trifluoromethyl and homologues), aralkyl (e.g., phenylalkyl or naphthylalkyl) as well as alkyl (i.e., unsubstituted alkyl) and aryl substituents such as phenylalkyl, phenyl, naphthyl, alkylphenyl, cyanophenyl, halophenyl, and alkoxyphenyl. Although the number of carbon atoms can be varied widely, commonly the E position substituent contains from about 1 to 18 carbon atoms, with individual alkyl moieties typically having from about 1 to 8 carbon atoms. In a specifically preferred form the entire E position substituent contains from 8 or fewer carbon atoms.

When the thiocarbonyl group —C(S)— is linked to an oxy group—e.g., $R^4$—O—, the resulting group is an oxythioamido group. When the thiocarbonyl group —C(S)— is linked to a thio group—e.g., $R^4$—S—, the resulting group is a dithioamido group. As between E and E', it is generally preferred that —O— or —S— occupy the E position. Adsorption promoting groups which correspond to —S— in the E position are disclosed by Mifune et al U.S. Pat. No. 4,243,739. Adsorption promoting groups containing —O— in the E position are preferred over their —S— analogues.

When E or E' and $R^4$ together form a heterocyclic ring, the ring is preferably a five or six-membered heterocyclic ring. Preferred rings formed by E' and $R^4$ are those found as acidic nuclei in merocyanine dyes. Specific illustrative ring structures are 4-thiazoline-2-thione, thiazolidine-2-thione, 4-oxazoline-2-thione, oxazolidine-2-thione, 2-pyrazoline-5-thione, 4-imidazoline-2-thione, 2-thiohydantoin, rhodanine, isorhodanine, 2-thio-2,4-oxazolidinedione, and thiobarbituric acid, which can, of course, be further substituted. Useful ring structures of this type are specifically illustrated in Leone et al U.S. Pat. No. 4,080,207. When E and $R^4$ together form a heerocyclic ring, the ring is preferably a 5 or 6 membered heterocyclic ring similar to those completed by Z described above, although the ring nitrogen atom need not be quaternized.

It is possible to attach the adsorption promoting moiety directly to Z or the organic ballast $R^3$ or through an intervening divalent linking group. Typical useful intervening divalent linking groups are illustrated by Hirano et al U.S. Pat. No. 4,255,511, Mifune et al U.S. Pat. No. 4,272,614, and Sidhu et al *Research Disclosure* Item 17626, cited above.

In one specific preferred form adsorption promoting moiety and alkynyl substituted heterocyclic quaternary ammonium salts according to this invention can be represented by the following formula:

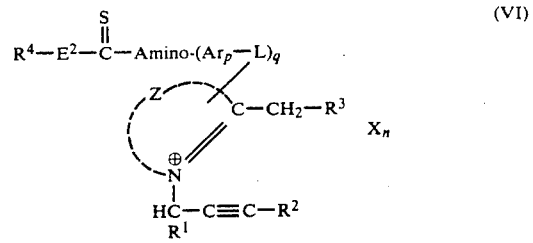

wherein
$E^2$ is —O— or —N($R^6$)—;
Ar is an arylene group;
L is a divalent aliphatic linking group;
p and q are 0 or 1; and
Amino, $R^1$, $R^2$, $R^3$, $R^4$, $R^6$, X, Z, and n are as previously described;

The divalent linking group can be employed to allow the Amino group to take a wider range of substituted forms than when ring attachment is directly through this group. For example, it is possible for the Amino group to take independently any of the forms described above for $R^6$ when the divalent linking group is present. The divalent linking group otherwise merely adds to the bulk of the compound without signicantly altering its function. Therefore it is apparent that Ar and L can be independently selected from among conventional divalent aromatic and aliphatic groups, respectively, such as those in conventional organic ballasting groups, and in a specifically preferred form q is 0 and no divalent linking group —(Ar$_p$—L)— is present.

The preparation of alkynyl substituted heterocyclic quaternary ammonium salts can be achieved as taught by Adachi et al U.S. Pat. No. 4,115,122, cited above, and is further illustrated in the Examples below. The attachment of an adsorption promoting moiety to an alkynyl substituted heterocyclic quaternary ammonium salt is also illustrated in the Examples.

One illustrative method for attaching an adsorption promoting moiety in which R$^4$ is an alkyl substituent can be represented by the following formula:

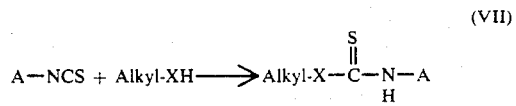
(VII)

where

A is an alkynyl substituted azolium or azinium nucleus;

E is as previously defined; and

Alkyl is an alkyl substituent.

The reaction is driven by heating to reflux. The isothiocyanato moiety can be attached to A by reaction of an amino substituted derivative of A with thiocarbonyldiimidazole.

Another, more general method of attaching adsorption promoting moieties can be represented by the following formula:

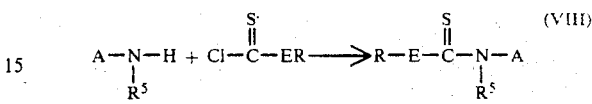
(VIII)

where

A, E, and R$^5$ are as previously defined.

The reaction proceeds at room temperature in the presence of a base, such as pyridine.

The following are illustrative of specific preferred thioamido and alkynyl substituted heterocyclic quaternary ammonium salts useful in the practice of this invention:

TABLE I $$R^4-E-\overset{\overset{S}{\|}}{C}-\underset{\underset{R^5}{|}}{N}-A$$

| Compound | E | R$^4$ | R$^5$ | A | |
|---|---|---|---|---|---|
| A | O | C$_2$H$_5$ | H | [naphthothiazolium with N-CH$_2$C≡CH, CH$_3$] | CF$_3$SO$_3^\ominus$ |
| B | O | C$_2$H$_5$ | H | [benzothiazolium with N-CH$_2$C≡CH, CH$_3$] | CF$_3$SO$_3^\ominus$ |
| C | NH | C$_6$H$_5$ | H | [benzothiazolium with N-CH$_2$C≡CH, CH$_3$] | I$^\ominus$ |
| D | NCH$_3$ | C$_6$H$_5$ | H | " | ClO$_4^\ominus$ |
| E+ | | | | [tetrazole-substituted benzothiazolium with N-CH$_2$C≡CH, CH$_3$] | ClO$_4^\ominus$ |

TABLE I-continued $$R^4-E-\overset{\overset{S}{\|}}{C}-\underset{\underset{R^5}{|}}{N}-A$$

| Compound | E | R⁴ | R⁵ | A | |
|---|---|---|---|---|---|
| F | NH | C₆H₅ | H | (2-methyl-1-propargyl quinolinium) | I⊖ |
| G | NCH₃ | C₆H₅ | H | " | ClO₄⊖ |
| H⁺ | | | | (1-H-tetrazol-5-thione linked to 2-methyl-1-propargyl quinolinium via phenyl) | ClO₄⊖ |
| I | NCH₃ | C₆H₅ | H | (5,6-dichloro-2-methyl-1-benzyl-3-propargyl benzimidazolium) | ClO₄⊖ |
| J | O | C₂H₅ | H | " | Br⊖ |
| K⁺* | | | | (8-methyl-2-methyl-1-propargyl quinolinium) | Br⊖ |
| L⁺* | | | | (6-chloro-2-methyl-1-propargyl quinolinium) | Br⊖ |
| M⁺* | | | | (2-methyl-1-propargyl quinolinium) | Br⊖ |

⁺Not segmented into individual moieties.
*This compound does not form a part of the invention, but is listed to show the structural similarity of the control compound employed in the examples.

Advantages in photographic performance can be realized by using the thioamido and alkynyl substituted heterocyclic ammonium salts described above so that they are present during development using an aqueous alkaline processing solution with radiation sensitive silver halide emulsions which form latent images either on their surface or internally by the photoelectron reduction of silver ions to silver atoms. Thus, apart from a few specialized silver halide photographic systems, such as photobleach reversal systems and those systems which require dry processing, the thioamido and alkynyl substituted heterocyclic ammonium salts are generally useful with silver halide photographic systems. Such systems and their component features are generally disclosed in *Research Disclosure,* Vol. 176, December 1978, Item 17643, here incorporated by reference.

It is specifically contemplated that the thioamido and alkynyl substituted heterocyclic ammonium salts of the present invention can be employed alone or in combination with conventional similarly useful quaternary ammonium salts, hydrazines, hydrazides, and hydrazones, such as those illustrated by Whitmore U.S. Pat. No. 3,227,552, Leone et al U.S. Pat. Nos. 4,030,925, 4,031,127, 4,080,207, Takada et al U.S. Pat. Nos. 4,168,977 and 4,224,401, Tsujino et al U.S. Pat. No. 4,245,037, Hirano et al 4,255,511, Adachi et al U.S. Pat. Nos. 4,115,122 and 4,266,013, Nothnagle U.S. Pat. No. 4,269,929, Mifune et al U.S. Pat. Nos. 4,243,739, 4,272,614, and 4,323,643, Leone U.S. Pat. No. 4,276,364, *Research Disclosure,* Items 15162 and 17626, cited above, Lincoln et al U.S. Pat. Nos. 3,615,615 and 3,854,956, Kurtz et al U.S. Pat. Nos. 3,719,494 and 3,734,738, von Konig et al U.S. Pat. No. 4,139,387, Baralle et al U.S. Pat. Nos. 4,306,016, 4,306,017, and 4,315,986, and U.K. Pat. Nos. 2,011,391, 2,012,443, and 2,087,057. These compounds can be employed in any photographically useful concentration, such as in previously taught concentrations, typically up to $10^{-2}$ mole per mole of silver.

These compounds can be incorporated in the silver halide emulsion by conventional procedures for incorporating photographic addenda, such as those set forth in *Research Disclosure,* Item 17643, cited above, Section XIV, here incorporated by reference. Where the compound is to be adsorbed to the surface of the silver halide grains, as is the case with the thioamido and alkynyl substituted heterocyclic ammonium salts of this invention, it can be adsorbed using the procedures well known to those skilled in the art for adsorbing sensitizing dyes, such as cyanine and merocyanine dyes, to the surface of silver halide grains. While it is preferred to incorporate the thioamido and alkynyl substituted heterocyclic ammonium salts directly in the silver halide emulsions prior to coating to form a photographic element, it is recognized that these salts are effective if incorporated at any time before development of an imagewise exposed photographic element.

Preferred silver halide emulsions and photographic elements incorporating the thioamido and alkynyl substituted heterocyclic ammonium salts of this invention are illustrated by two differing photographic systems discussed below.

Direct Positive Imaging

Photographic elements which produce images having an optical density directly related to the radiation received on exposure are said to be negative working. A positive photographic image can be formed by producing a negative photographic image and then forming a second photographic image which is a negative of the first negative, that is, a positive image. A direct positive image is understood in photography to be a positive image that is formed without first forming a negative image. Positive dye images which are not direct positive images are commonly produced in color photography by reversal processing in which a negative silver image is formed and a complementary positive dye image is then formed in the same photographic element. The term "direct reversal" has been applied to direct positive photographic elements and processing which produces a positive dye image without forming a negative silver image. Direct positive photography in general and direct reversal photography in particular are advantageous in providing a more straightforward approach to obtaining positive photographic images.

The thioamido and alkynyl substituted heterocyclic ammonium salts can be employed as nucleating agents with any conventional photographic element capable of forming a direct positive image containing, coated on a photographic support, at least one silver halide emulsion layer containing a vehicle and silver halide grains capable of forming an internal latent image upon exposure to actinic radiation. As employed herein, the terms "internal latent image silver halide grains" and "silver halide grains capable of forming an internal latent image" are employed in the art-recognized sense of designating silver halide grains which produce substantially higher optical densities when coated, imagewise exposed, and developed in an internal developer than when comparably coated, exposed and developed in a surface developer. Preferred internal latent image silver halide grains are those which, when examined according to normal photographic testing techniques, by coating a test portion on a photographic support (e.g., at a coverage of from 3 to 4 grams per square meter), exposing to a light intensity scale (e.g., with a 500-watt tungsten lamp at a distance of 61 cm) for a fixed time (e.g., between $1 \times 10^{-2}$ and 1 second) and developing for 5 minutes at 25° C. in Kodak Developer DK-50 (a surface developer), provide a density of at least 0.5 less than when this testing procedure is repeated, substituting for the surface developer Kodak Developer DK-50 containing 0.5 gram per liter of potassium iodide (an internal developer). The internal latent image silver halide grains most preferred for use in the practice of this invention are those which, when tested using an internal developer and a surface developer as indicated above, produce an optical density with the internal developer at least 5 times that produced by the surface developer. It is additionally preferred that the internal latent image silver halide grains produce an optical density of less than 0.4 and, most preferably, less than 0.25 when coated, exposed and developed in surface developer as indicated above, that is, the silver halide grains are preferably initially substantially unfogged and free of latent image on their surface.

The surface developer referred to herein as Kodak Developer DK-50 is described in the *Handbook of Chemistry and Physics,* 30th edition, 1947, Chemical Rubber Publishing Company, Cleveland, Ohio, page 2558, and has the following composition:

| | |
|---|---|
| Water, about 125° F. (52° C.) | 500.0 cc |
| N—methyl-p-aminophenol hemisulfate | 2.5 g |
| Sodium sulfite, desiccated | 30.0 g |
| Hydroquinone | 2.5 g |
| Sodium metaborate (with four molecules of water) | 10.0 g |

| | |
|---|---|
| -continued | |
| Potassium bromide | 0.5 g |
| Water to make | 1.0 liter. |

Internal latent image silver halide grains which can be employed in the practice of this invention are well known in the art. Patents teaching the use of internal latent image silver halide grains in photographic emulsions and elements include Davey et al U.S. Pat. No. 2,592,250, Porter et al U.S. Pat. No. 3,206,313, Milton U.S. Pat. No. 3,761,266, Ridgway U.S. Pat. No. 3,586,505, Gilman et al U.S. Pat. No. 3,772,030, Gilman et al U.S. Pat. No. 3,761,267, and Evans U.S. Pat. No. 3,761,276, the disclosures of which are hereby incorporated by reference.

It is specifically preferred to employ high aspect ratio tabular grain internal latent image forming emulsions. Such emulsions are the specific subject matter of Evans et al U.S. Ser. No. 431,912, filed Sept. 30, 1982, commonly assigned, titled DIRECT REVERSAL EMULSIONS AND PHOTOGRAPHIC ELEMENTS USEFUL IN IMAGE TRANSFER FILM UNITS, now abandoned in favor of U.S. Ser. No. 564,976, filed Dec. 23, 1983. These emulsions are also disclosed in Research Disclosure, Vol. 225, January 1983, Item 22534.

The internal latent image silver halide grains preferably contain bromide as the predominant halide. The silver bromide grains can consist essentially of silver bromide or can contain silver bromoiodide, silver chlorobromide, silver chlorobromoiodide crystals and mixtures thereof. Internal latent image forming sites can be incorporated into the grains by either physical or chemical internal sensitization. Davey et al, cited above, for example, teaches the physical formation of internal latent image forming sites by the halide conversion technique. Chemical formation of internal latent image forming sites can be produced through the use of sulfur, gold, selenium, tellurium and/or reduction sensitizers of the type described, for example, in Sheppard et al U.S. Pat. No. 1,623,499, Waller et al U.S. Pat. No. 2,399,083, McVeigh U.S. Pat. No. 3,297,447, and Dunn U.S. Pat. No. 3,297,446, as taught in the patents cited in the preceding paragraph. Internal latent image sites can also be formed through the incorporation of metal dopants, particularly Group VIII noble metals, such as ruthenium, rhodium, palladium, iridium, osmium and platinum, as taught by Berriman U.S. Pat. No. 3,367,778. The preferred foreign metal ions are polyvalent metal ions which include the above noted Group VIII dopants, as well as polyvalent metal ions such as lead, antimony, bismuth, and arsenic. In a preferred approach, the internal latent image sites can be formed within the silver halide grains during precipitation of silver halide. In an alternate approach, a core grain can be formed which is treated to form the internal image sites and then a shell deposited over the core grains, as taught by Porter et al, cited above.

The silver halide grains employed in the practice of this invention are preferably monodispersed and in some embodiments are preferably large grain emulsions made according to Wilgus German OLS 2,107,118, which is incorporated herein by reference. The monodispersed emulsions are those which comprise silver halide grains having a substantially uniform diameter. Generally, in such emulsions, no more than about 5 percent by number of the silver halide grains smaller than the mean grain size and/or no more than about 5 percent by number of the silver halide grains larger than the mean grain size vary in diameter from the mean grain diameter by more than about 40 percent. Preferred photographic emulsions of this invention comprise silver halide grains, at least 95 percent by weight of said grains having a diameter which is within 40 percent and preferably within about 30 percent of the mean grain diameter. Mean grain diameter, i.e., average grain size, can be determined using conventional methods, e.g., such as projective area, as shown in an article by Trivelli and Smith entitled "Empirical Relations Between Sensitometric and Size-Frequency Characteristics in Photographic Emulsion Series" in *The Photographic Journal*, Volume LXXIX, 1939, pages 330 through 338. The aforementioned uniform size distribution of silver halide grains is a characteristic of the grains in monodispersed photographic silver halide emulsions. Silver halide grains having a narrow size distribution can be obtained by controlling the conditions at which the silver halide grains are prepared using a double run procedure. In such a procedure, the silver halide grains are prepared by simultaneously running an aqueous solution of a silver salt, such as silver nitrate, and an aqueous solution of a water soluble halide, for example, an alkali metal halide such as potassium bromide, into a rapidly agitated aqueous solution of a silver halide peptizer, preferably gelatin, a gelatin derivative or some other protein peptizer. Suitable methods for preparing photographic silver halide emulsions having the required uniform particle size are disclosed in an article entitled "Ia: Properties of Photographic Emulsion Grains", by Klein and Moisar, *The Journal of Photographic Science*, Volume 12, 1964, pages 242 through 251; an article entitled "The Spectral Sensitization of Silver Bromide Emulsions on Different Crystallographic Faces", by Markocki, *The Journal of Photographic Science*, Volume 13, 1965, pages 85 through 89; an article entitled "Studies on Silver Bromide Sols, Part I. The Formation and Aging of Monodispersed Silver Bromide Sols", by Ottewill and Woodbridge, *The Journal of Photographic Science*, Volume 13, 1965, pages 98 through 103; and an article entitled "Studies on Silver Bromide Sols, Part II. The Effect of Additives on the Sol Particles", by Ottewill and Woodbridge, *The Journal of Photographic Science*, Volume 13, 1965, pages 104 through 107.

Where internal latent image sites have been formed through internal chemical sensitization or the use of metal dopants, the surface of the silver halide grains can be sensitized to a level below that which will produce substantial density in a surface developer, that is, less than 0.4 (preferably less than 0.25) when coated, exposed and surface developed as described above. The silver halide grains are preferably predominantly silver bromide grains chemically surface sensitized to a level which would provide a maximum density of at least 0.5 using undoped silver halide grains of the same size and halide composition when coated, exposed and developed as described above.

The silver halide emulsion can be unwashed or washed to remove soluble salts. The soluble salts can be removed by chill setting and leaching, as illustrated by Craft U.S. Pat. No. 2,316,845 and McFall et al U.S. Pat. No. 3,396,027; by coagulation washing, as illustrated by Hewitson et al U.S. Pat. No. 2,618,556, Yutzy et al U.S. Pat. No. 2,614,928, Yackel U.S. Pat. No. 2,565,418, Hart et al U.S. Pat. No. 3,241,969, Waller et al U.S. Pat. No. 2,489,341, Klinger U.K. Pat. No. 1,305,409 and Dersch et al U.K. Pat. No. 1,167,159; by centrifugation and decantation of a coagulated emulsion, as illustrated by Murray U.S. Pat. No. 2,463,794, Ujihara et al U.S. Pat. No. 3,707,378, Audran U.S. Pat. Nos. 2,996,287 and Timson U.S. Pat. No. 3,498,454; by employing hydrocyclones alone or in combination with centrifuges, as illustrated by U.K. Pat. No. 1,336,692, Claes U.K. Pat. No. 1,356,573 and Ushomirskii et al *Soviet Chemical Industry*, Vol. 6, No. 3, 1974, pages 181-185; by diafiltration with a semipermeable membrane, as illustrated by *Research Disclosure*, Vol. 102, October 1972, Item 10208, Hagemaier et al *Research Disclosure*, Vol. 131, March 1975, Item 13122, Bonnet *Research Disclosure*, Vol. 135, July 1975, Item 13577, Berg et al German OLS 2,436,461 and Bolton U.S. Pat. No. 2,495,918 or by employing an ion exchange resin, as illustrated by Maley U.S. Pat. No. 3,782,953 and Noble U.S. Pat. No. 2,827,428. The emulsions, with or without sensitizers, can be dried and stored prior to use as illustrated by *Research Disclosure*, Vol. 101, September 1972, Item 10152.

Although surface chemical sensitization of internal latent image forming silver halide emulsion grains is not necessary, highest speeds are obtained when surface chemical sensitization is undertaken, but limited to retain a balance of surface and internal sensitivity favoring the formation of an internal latent image. Surface chemical sensitization can be undertaken using techniques such as those disclosed by Sheppard, Waller et al, McVeigh, or Dunn, cited above. The silver halide grains can also be surface sensitized with salts of the noble metals, such as ruthenium, palladium and platinum. Representative compounds are ammonium chloropalladate, potassium chloroplatinate and sodium chloropalladate, which are used for sensitizing in amounts below that which produces any substantial fog inhibition, as described in Smith et al U.S. Pat. No. 2,448,060, and as antifoggants in higher amounts, as described in Trivelli et al U.S. Pat. Nos. 2,566,245 and 2,566,263. The silver halide grains can also be chemically sensitized with reducing agents, such as stannous salts (Carroll U.S. Pat. No. 2,487,850, polyamines, such as diethylene triamine (Lowe et al U.S. Pat. No. 2,518,698), polyamines, such as spermine (Lowe et al U.S. Pat. No. 2,521,925), or bis-($\beta$-aminoethyl)sulfide and its water soluble salts (Lowe et al U.S. Pat. No. 2,521,926).

Photographic emulsion layers, and other layers of photographic elements, such as overcoat layers, interlayers, and subbing layers, as well as receiving layers in image transfer elements, can also contain as vehicles water permeable hydrophilic colloids as vehicles alone or in combination with vehicle extenders (e.g., in the form of latices), such as synthetic polymeric peptizers, carriers and/or binders. Such materials are more specifically described in *Research Disclosure*, Item 17643, cited above, Section IX. Vehicles are commonly employed with one or more hardeners, such as those described in Section X.

The layers of the photographic elements can be coated on any conventional photographic support. Typical useful photographic supports are disclosed in *Research Disclosure*, Item 17643, cited above, Section XVII.

A simple exposure and development process can be used to form a direct positive image. In one embodiment, a photographic element comprising at least one layer of a silver halide emulsion as described above can be imagewise exposed to light and then developed in a silver halide surface developer.

It is understood that the term "surface developer" encompasses those developers which will reveal the surface latent image on a silver halide grain, but will not reveal substantial internal latent image in an internal image forming emulsion, and under the conditions generally used develop a surface sensitive silver halide emulsion. The surface developers can generally utilize any of the silver halide developing agents or reducing agents, but the developing bath or composition is generally substantially free of a silver halide solvent (such as water soluble thiocyanates, water soluble thioethers, thiosulfates, and ammonia) which will disrupt or dissolve the grain to reveal substantial internal image. Low amounts of excess halide are sometimes desirable in the developer or incorporated in the emulsion as halide releasing compounds, but high amounts of iodide or iodide releasing compounds are generally avoided to prevent substantial disruption of the grain. Typical silver halide developing agents which can be used in the developing compositions employed with this invention include hydroquinones, catechols, aminophenols, 3-pyrazolidones, ascorbic acid and its derivatives, reductones and color developing agents, that is, primary aromatic amine developing agents, such as, aminophenols and paraphenylenediamines. The color developing agents are preferably employed in combination with black-and-white developing agents capable of acting as electron transfer agents. Illustrative of useful surface developers are those disclosed in Ives U.S. Pat. No. 2,563,785, Evans U.S. Pat. No. 3,761,276, Knott et al U.S. Pat. No. 2,456,953, and Juoy U.S. Pat. No. 3,511,662.

Where the developing agents are initially entirely incorporated in the photographic elements, the remaining components (e.g., water, activators to adjust pH, preservatives, etc.) normally present in surface developers constitute what is commonly referred to as an activator solution. Except for the omission of the developing agent, activator solutions are identical to developer solutions in composition and are employed identically with incorporated developing agent photographic elements. Subsequent references to developing compositions are inclusive of both developer and activator solutions.

The surface developers are alkaline. Conventional activators, preferably in combination with buffers, such as, sodium hydroxide, potassium hydroxide, sodium carbonate, potassium carbonate, trisodium phosphate or sodium metaphosphate, can be employed to adjust pH to a desired alkaline level. The amounts of these materials are selected so as to adjust the developer to the desired pH. The thioamido substituted alkynyl heterocyclic ammonium salts of this invention are generally useful over the same pH ranges as conventional alkynyl heterocyclic ammonium salts. The preferred pH is typically within the range of from 10 to 14, most preferably from about 10.5 to 13.

The developing compositions can contain certain antifoggants and development restrainers, or, optionally, they can be incorporated in layers of the photographic element. For example, in some applications, improved results can be obtained when the direct positive emulsions are processed in the presence of certain antifoggants, as disclosed in Stauffer U.S. Pat. No. 2,497,917, Land U.S. Pat. No. 2,704,721, Rogers et al U.S. Pat. No. 3,265,498, and Baldassari et al U.S. Pat.

No. 3,925,086, which are incorporated herein by reference.

Preferred antifoggants are benzotriazoles, such as, benzotriazole (that is, the unsubstituted benzotriazole compound), halo-substituted benzotriazoles (e.g., 5-chlorobenzotriazole, 4-bromobenzotriazole, and 4-chlorobenzotriazole), and alkyl-substituted benzotriazoles wherein the alkyl moiety contains from about 1 to 12 carbon atoms (e.g., 5-methylbenzotriazole). Other known useful antifoggants include benzimidazoles, such as 5-nitrobenzimidazole, benzothiazoles, such as 5-nitrobenzothiazole and 5-methylbenzothiazole, heterocyclic thiones, such as 1-methyl-2-tetrazoline-5-thione, triazines, such as 2,4-dimethylamino-6-chloro-5-triazine, benzoxazoles, such as ethylbenzoxazole, and pyrroles, such as 2,5-dimethylpyrrole and the like.

Improved results are obtained when the element is processed in the presence of the antifoggants mentioned above. The antifoggants can be present in the processing solution during development or incorporated in the photographic element. It is preferred to incorporate the antifoggant in the processing solution.

It is specifically contemplated that the thioamido and alkynyl substituted heterocyclic ammonium salt nucleating agents of the present invention can be employed alone or in combination with conventional nucleating agents, such as those of the quaternary ammonium salt, hydrazine, hydrazide, and hydrazone type previously identified. The nucleating agents can be incorporated in the photographic elements in previously taught concentrations, typically up to $10^{-2}$ mole per mole of silver. It is preferred to incorporate the thioamido and alkynyl substituted heterocyclic ammonium salt nucleating agents in concentrations of from $10^{-5}$ to $10^{-2}$ mole per mole of silver with a preferred concentration being from $10^{-5}$ to $10^{-3}$ mole per mole of silver.

The essential features of the thioamido and alkynyl substituted heterocyclic quaternary ammonium salt nucleating agents of this invention and the direct positive silver halide emulsions and photographic elements in which they are incorporated, as well as procedures for their use and processing, are described above. It is appreciated that, in preferred photographic applications, the emulsions and elements can contain additional features which are in themselves well known to those familiar with the photographic art, such as those disclosed in *Research Disclosure*, Item 17643, cited above and here incorporated by reference. Certain specifically preferred features are described below.

The silver halide emulsions can be spectrally sensitized with cyanine, merocyanine, and other polymethine dyes and supersensitizing combinations thereof well known in the art. Spectral sensitizers in conventional surface sensitive emulsions are comparably effective in the emulsions of this invention. In general, they enhance nucleation. Nonionic, zwitterionic and anionic spectral sensitizers are preferred. Particularly effective are carboxy substituted merocyanine dyes of the thiohydantoin type described by Stauffer et al U.S. Pat. No. 2,490,758.

Effective red sensitizers are the carbocyanines of formula (IX)

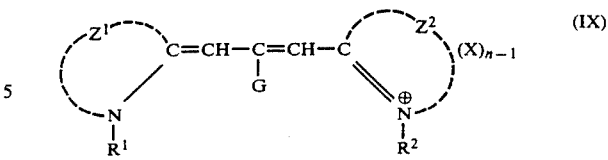

wherein each of $Z^1$ and $Z^2$ represents the atoms necessary to form a benzothiazole, benzoselenazole, naphthothiazole, or naphthoselenazole, the benzothiazole and benzoselenazole being preferably 5- and/or 6-substituted with groups such as lower alkyl, lower alkoxy, chloro, bromo, fluoro, hydroxy, acylamino, cyano, and trifluoromethyl, G represents hydrogen and lower alkyl, preferably ethyl or methyl, each of $R^1$ and $R^2$ represents lower alkyl or hydroxy(lower)alkyl, at least one of $R^1$ and $R^2$ being preferably acid substituted(lower)alkyl, such as, carboxyethyl, sulfopropyl, and sulfatoethyl, X represents a charge balancing counter ion, and n is 1 or 2.

Particularly effective are certain super-sensitizing combinations of the above dyes with each other and with dyes or other adsorbed organic compounds having polarographic oxidation potentials ($E_{ox}$) of about 0.3 to 0.9 volt. Many such combinations are described in Mees U.S. Pat. No. 2,075,048, Carroll et al U.S. Pat. Nos. 2,313,922, 2,533,426, 2,688,545, and 2,704,714, Jones U.S. Pat. No. 2,704,717, and Schwan 3,672,898, and include, as well, the acid substituted analogues thereof well known in the art.

Effective green sensitizers are carbocyanines and cyanines of formulae (X) and (XI)

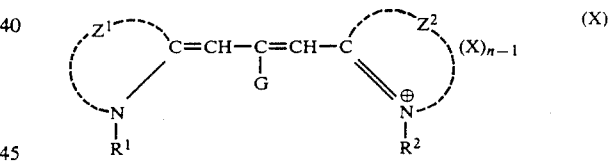

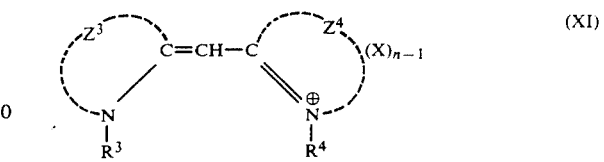

wherein each of $Z^1$ and $Z^2$ represents the atoms necessary to form benzoxazole and benzimidazole nuclei, benzimidazole being substituted in the 3-position by lower alkyl or aryl, and preferably in the 5- and/or 6-positions with groups selected from fluoro, chloro, bromo, lower alkyl, cyano, acylamino and trifluoromethyl, and the benzoxazole ring preferably substituted in the 5- or 6-positions with lower alkyl, lower alkoxy, phenyl, fluoro, chloro, and bromo, $Z^3$ represents the atoms necessary to form benzothiazole, benzoselenazole, naphthothiazole, naphthoselenazole, or 2-quinoline, $Z^4$ represents the atoms necessary to form 2-quinoline, G represents lower alkyl and, if at least one of $Z^1$ and $Z^2$ forms benzimidazole, hydrogen, each of $R^1$, $R^2$, $R^3$ and $R^4$ represents lower alkyl or hydroxy(lower)alkyl, at least one of $R^1$ and $R^2$ and of $R^3$ and $R^4$ being preferably acid substituted (lower) alkyl such as carboxyethyl, sulfopropyl, and sulfatoethyl, X represents a charge balancing counter ion, and n is 1 or 2.

Particularly effective are certain supersensitizing combinations of the above dyes, such as those described in Carroll et al U.S. Pat. Nos. 2,688,545 and 2,701,198, Nys et al U.S. Pat. No. 2,973,264, and Schwan et al U.S. Pat. No. 3,397,069 and their acid substituted analogues well known in the art.

Effective blue sensitizers are simple cyanines and merocyanines of formulae (XII) and (XIII)

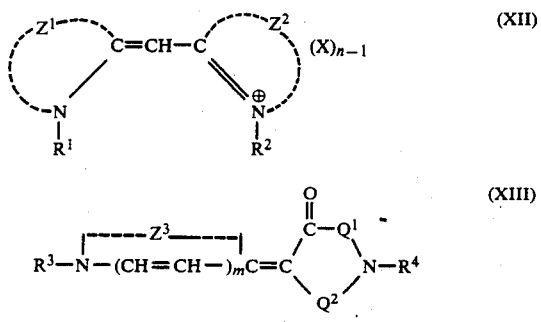

wherein each of $Z^1$ and $Z^2$ represents the atoms necessary to form benzothiazole, benzoselenazole, naphthothiazole and naphthoselenazole nuclei which may be substituted with groups such as chloro, methyl or methoxy, chloro, bromo, lower alkyl, or lower alkoxy, $Z^3$ represents benzothiazole, benzoselenazole which may be substituted as in $Z^1$ and $Z^2$, and a pyridine nucleus, $Q^1$ and $Q^2$ together represent the atoms necessary to complete a rhodanine, 2-thio-2,4-oxazolidinedione or 2-thiohydantoin ring, the latter having a second nitrogen atom with a substituent $R^5$, m represents 0 or 1, each of $R^1$, $R^2$ and $R^3$ represents lower alkyl or hydroxy(lower)alkyl, at least one of $R^1$ and $R^2$ being preferably acid substituted(lower)alkyl such as carboxyethyl, sulfopropyl, and sulfatoethyl, $R^4$ and $R^5$ represent lower alkyl and hydroxy (lower)alkyl, and $R^4$ additionally can represent carboxyalkyl and sulfoalkyl, X is a charge balancing counter ion, and n is 1 or 2.

(Lower alkyl in each occurrence of Formulas IX to XIII includes from 1 to 5 carbon atoms.)

In one preferred form the photographic elements can produce silver images. Specifically preferred photographic elements for producing silver images are those disclosed in Evans et al U.S. Ser. No. 431,912, cited above, and Hoyen and Silverman U.S. Pat. Nos. 4,444,865 and 4,444,874, each filed Sept. 30, 1982, commonly assigned and here incorporated by reference. In another preferred form the photographic elements can be color photographic elements which form dye images through the selective destruction, formation or physical removal of dyes.

The photographic elements can produce dye images through the selective destruction of dyes or dye precursors, such as silver-dye-bleach processes, as illustrated by A. Meyer, *The Journal of Photographic Science*, Volume 13, 1965, pages 90 through 97. Bleachable azo, azoxy, xanthene, azine, phenylmethane, nitroso complex, indigo, quinone, nitro substituted, phthalocyanine and formazan dyes, as illustrated by Stauner et al U.S. Pat. No. 3,754,923, Piller et al U.S. Pat. No. 3,749,576, Yoshida et al U.S. Pat. No. 3,738,839, Froelich et al U.S. Pat. No. 3,716,368, Piller U.S. Pat. No. 3,655,388, Williams et al U.S. Pat. No. 3,642,482, Gilman U.S. Pat. No. 3,567,448, Loeffel U.S. Pat. No. 3,443,953, Anderau U.S. Pat. Nos. 3,443,952 and 3,211,556, Mory et al U.S. Pat. Nos. 3,202,511 and 3,178,291, and Anderau et al U.S. Pat. Nos. 3,178,285 and 3,178,290 as well as their hydrazo, diazonium, and tetrazolium precursors and leuco and shifted derivatives, as illustrated by U.K. Pat. Nos. 923,265, 999,996, and 1,042,300, Pelz et al U.S. Pat. No. 3,684,513, Watanabe et al U.S. Pat. No. 3,615,493, Wilson et al U.S. Pat. No. 3,503,741, Boes et al U.S. Pat. No. 3,340,059, Gompf et al U.S. Pat. No. 3,493,372, and Puschel et al U.S. Pat. No. 3,561,970 can be employed.

The photographic elements can produce dye images through the selective formation of dyes, such as by reacting (coupling) a color developing agent (e.g., a primary aromatic amine) in its oxidized form with a dye forming coupler. The dye forming couplers can be incorporated in the photographic elements, as illustrated by Schneider et al, *Die Chemie*, Volume 57, 1944, page 113, Mannes et al U.S. Pat. No. 2,304,940, Martinez U.S. Pat. No. 2,269,158, Jelley et al U.S. Pat. No. 2,322,027, Frolich et al U.S. Pat. No. 2,376,679, Fierke et al U.S. Pat. No. 2,801,171, Smith U.S. Pat. No. 3,748,141, Tong U.S. Pat. No. 2,772,163, Thirtle et al U.S. Pat. No. 2,835,579, Sawdey et al U.S. Pat. No. 2,533,514, Peterson U.S. Pat. No. 2,353,754, Seidel U.S. Pat. No. 3,409,435, and Chen *Research Disclosure*, Volume 159, July 1977, Item 15930.

In one form, the dye forming couplers are chosen to form subtractive primary (i.e., yellow, magenta, and cyan) image dyes and are nondiffusible, colorless couplers, such as, two- and four-equivalent couplers of the open chain ketomethylene, pyrazolone, pyrazolotriazole, pyrazolobenzimidazole, phenol, and naphthol type hydrophobically ballasted for incorporation in high-boiling organic (coupler) solvents. Such couplers are illustrated by Salminen et al U.S. Pat. Nos. 2,423,730, 2,772,162, 2,895,826, 2,710,803, 2,407,207, 3,737,316, and 2,367,531, Loria et al U.S. Pat. Nos. 2,772,161, 2,600,788, 3,006,759, 3,214,437, and 3,253,924, McCrossen et al U.S. Pat. No. 2,875,057, Bush et al U.S. Pat. No. 2,908,573, Gledhill et al U.S. Pat. No. 3,034,892, Weissberger et al U.S. Pat. Nos. 2,474,293, 2,407,210, 3,062,653, 3,265,506, and 3,384,657, Porter et al U.S. Pat. No. 2,343,703, Greenhalgh et al U.S. Pat. No. 3,127,269, Feniak et al U.S. Pat. Nos. 2,865,748, 2,933,391, and 2,865,751, Bailey et al U.S. Pat. No. 3,725,067, Beavers et al U.S. Pat. No. 3,758,308, Lau U.S. Pat. No. 3,779,763, Fernandez U.S. Pat. No. 3,785,829, U.K. Pat. No. 969,921, U.K. Pat. No. 1,241,069, U.K. Pat. No. 1,011,940, Vanden Eynde et al U.S. Pat. No. 3,762,921, Beavers U.S. Pat. No. 2,983,608, Loria U.S. Pat. Nos. 3,311,476, 3,408,194, 3,458,315, 3,447,928, and 3,476,563, Cressman et al U.S. Pat. No. 3,419,390, Young U.S. Pat. No. 3,419,391, Lestina U.S. Pat. No. 3,519,429, U.K. Pat. No. 975,928, U.K. Pat. No. 1,111,554, Jaeken U.S. Pat. No. 3,222,176 and Canadian Pat. No. 726,651, Schulte et al U.K. Pat. No. 1,248,924, and Whitmore et al U.S. Pat. No. 3,227,550.

The photographic elements can incorporate alkali soluble ballasted couplers, as illustrated by Froelich et al and Tong, cited above. The photographic elements can be adapted to form nondiffusible image dyes using dye forming couplers in developers, as illustrated by U.K. Pat. No. 478,984, Yager et al U.S. Pat. No. 3,113,864, Vittum et al U.S. Pat. Nos. 3,002,836, 2,271,238, and 2,362,598, Schwan et al U.S. Pat. No. 2,950,970, Carroll et al U.S. Pat. No. 2,592,243, Porter et al U.S. Pat. Nos. 2,343,703, 2,376,380, and 2,369,489, Spath U.K. Pat. No. 886,723 and U.S. Pat. No. 2,899,306, Tuite U.S. Pat. No. 3,152,896, and Mannes et al U.S. Pat. Nos. 2,115,394, 2,252,718, and 2,108,602.

The dye forming couplers upon coupling can release photographically useful fragments, such as development inhibitors or accelerators, bleach accelerators, developing agents, silver halide solvents, toners, hardeners, fogging agents, antifoggants, competing couplers, chemical or spectral sensitizers, and desensitizers. Development inhibitor releasing (DIR) couplers are illustrated by Whitmore et al U.S. Pat. No. 3,148,062, Barr et al U.S. Pat. No. 3,227,554, Barr U.S. Pat. No. 3,733,201, Sawdey U.S. Pat. No. 3,617,291, Groet et al U.S. Pat. No. 3,703,375, Abbott et al U.S. Pat. No. 3,615,506, Weissberger et al U.S. Pat. No. 3,265,506, Seymour U.S. Pat. No. 3,620,745, Marx et al U.S. Pat. No. 3,632,345, Mader et al U.S. Pat. No. 3,869,291, U.K. Pat. No. 1,201,110, Oishi et al U.S. Pat. No. 3,642,485, Verbrugghe U.K. Pat. No. 1,236,767, Fujiwhara et al U.S. Pat. No. 3,770,436, and Matsuo et al U.S. Pat. No. 3,808,945. DIR compounds which do not form dye upon reaction with oxidized color developing agents can be employed, as illustrated by Fujiwhara et al German OLS 2,529,350 and U.S. Pat. Nos. 3,928,041, 3,958,993, and 3,961,959, Odenwalder et al German OLS 2,448,063, Tanaka et al German OLS 2,610,546, Kikuchi et al U.S. Pat. No. 4,049,455, and Credner et al U.S. Pat. No. 4,052,213. DIR compounds which oxidatively cleave can be employed, as illustrated by Porter et al U.S. Pat. No. 3,379,529, Green et al U.S. Pat. No. 3,043,690, Barr U.S. Pat. No. 3,364,022, Duennebier et al U.S. Pat. No. 3,297,445, and Rees et al U.S. Pat. No. 3,287,129.

The photographic elements can incorporate colored dye forming couplers, such as those employed to form integral masks for negative color images, as illustrated by Hanson U.S. Pat. No. 2,449,966, Glass et al U.S. Pat. No. 2,521,908, Gledhill et al U.S. Pat. No. 3,034,892, Loria U.S. Pat. No. 3,476,563, Lestina U.S. Pat. No. 3,519,429, Friedman U.S. Pat. No. 2,543,691, Puschel et al U.S. Pat. No. 3,028,238, Menzel et al U.S. Pat. No. 3,061,432, and Greenhalgh U.K. Pat. No. 1,035,959, and/or competing couplers, as illustrated by Murin et al U.S. Pat. No. 3,876,428, Sakamoto et al U.S. Pat. No. 3,580,722, Puschel U.S. Pat. No. 2,998,314, Whitmore U.S. Pat. No. 2,808,329, Salminen U.S. Pat. No. 2,742,832, and Weller et al U.S. Pat. No. 2,689,793.

The photographic elements can produce dye images through the selective removal of dyes. Negative or positive dye images can be produced by the immobilization of incorporated color providing substances as a function of exposure and development, as illustrated by U.K. Pat. Nos. 1,456,413, 1,479,739, 1,475,265, and 1,471,752, Friedman U.S. Pat. No. 2,543,691, Whitmore U.S. Pat. No. 3,227,552, Bloom et al U.S. Pat. No. 3,443,940, Morse U.S. Pat. No. 3,549,364, Cook U.S. Pat. No. 3,620,730, Danhauser U.S. Pat. No. 3,730,718, Staples U.S. Pat. No. 3,923,510, Oishi et al U.S. Pat. No. 4,052,214, and Fleckenstein et al U.S. Pat. No. 4,076,529.

The photographic elements can contain antistain agents (i.e., oxidized developing agent scavengers) to prevent developing agents oxidized in one dye image layer unit from migrating to an adjacent dye image layer unit. Such antistain agents include ballasted or otherwise non-diffusing antioxidants, as illustrated by Weissberger et al U.S. Pat. No. 2,336,327, Loria et al U.S. Pat. No. 2,728,659, Vittum et al U.S. Pat. No. 2,360,290, Jelley et al U.S. Pat. No. 2,403,721, and Thirtle et al U.S. Pat. No. 2,701,197. To avoid autooxidation the antistain agents can be employed in combination with other antioxidants, as illustrated by Knechel et al U.S. Pat. No. 3,700,453.

The photographic elements can include image dye stabilizers. Such image dye stabilizers are illustrated by U.K. Pat. No. 1,326,889, Lestina et al U.S. Pat. Nos. 3,432,300 and 3,698,909, Stern et al U.S. Pat. No. 3,574,627, Brannock et al U.S. Pat. No. 3,573,050, Arai et al U.S. Pat. No. 3,764,337, and Smith et al U.S. Pat. No. 4,042,394.

This invention is particularly useful with photographic elements used in image transfer processes or in image transfer film units.

Image transfer systems include colloid transfer systems, as illustrated by Yutzy et al U.S. Pat. Nos. 2,596,756 and 2,716,059, silver salt diffusion transfer systems, as illustrated by Rott U.S. Pat. No. 2,352,014, Land U.S. Pat. No. 2,543,181, Yackel et al U.S. Pat. No. 3,020,155, and Land U.S. Pat. No. 2,861,885, imbibition transfer systems, as illustrated by Minsk U.S. Pat. No. 2,882,156, and color image transfer systems, as illustrated by *Research Disclosure*, Volume 151, November 1976, Item 15162, and Volume 123, July 1974, Item 12331.

Color image transfer systems (including emulsion layers, receiving layers, timing layers, acid layers, processing compositions, supports, and cover sheets) and the images they produce can be varied by choosing among a variety of features, combinations of which can be used together as desired.

Film units can be chosen which are either integrally laminated or separated during exposure, processing and/or viewing, as illustrated by Rogers U.S. Pat. No. 2,983,606, Beavers et al U.S. Pat. No. 3,445,228, Whitmore, Canadian Pat. No. 674,082, Friedman et al U.S. Pat. No. 3,309,201, Land U.S. Pat. Nos. 2,543,181, 3,053,659, 3,415,644, 3,415,645, and 3,415,646, and Barr et al U.K. Pat. No. 1,330,524.

A variety of approaches are known in the art for obtaining transferred dye images. The approaches can be generally categorized in terms of the initial mobility of dye or dye precursor. (Initial mobility refers to the mobility of the dye or dye precursor when it is contacted by the processing solution. Initially mobile dyes and dye precursors as coated do not migrate prior to contact with processing solution.)

Dye image providing compounds are classified as either positive working or negative working. Positive working dye image providing compounds are those which produce a positive transferred dye image when employed in combination with a conventional, negative working silver halide emulsion. Negative working dye image providing compounds are those which produce a negative transferred dye image when employed in combination with conventional, negative working silver halide emulsions. When, as in the present invention, the silver halide emulsions are direct positive emulsions, positive working dye image providing compounds produce negative transferred dye images and negative working dye image providing compounds produce positive transferred dye images.

Image transfer systems, which include both the dye image providing compounds and the silver halide emulsions, are positive working when the transferred dye image is positive and negative working when the transferred dye image is negative. When a retained dye image is formed, it is opposite in sense to the transferred dye image.

A variety of dye image transfer systems have been developed and can be employed in the practice of this invention. One approach is to employ ballasted dye forming (chromogenic) or nondye forming (nonchromogenic) couplers having a mobile dye attached at a coupling-off site. Upon coupling with an oxidized color developing agent, such as a para-phenylenediamine, the mobile dye is displaced so that it can transfer to a receiver. This negative working image transfer approach is illustrated by Whitmore et al U.S. Pat. No. 3,227,550, Whitmore U.S. Pat. No. 3,227,552, and Fujihara et al U.K. Pat. No. 1,445,797, the disclosures of which are here incorporated by reference.

In a preferred image transfer system according to this invention employing negative working dye image providing compounds, a cross oxidizing developing agent (electron transfer agent) develops silver halide and then cross oxidizes with a compound containing a dye linked through an oxidizable sulfonamido group, such as a sulfonamidophenol, sulfonamidoaniline, sulfonamidoanilide, sulfonamidopyrazolobenzimidazole, sulfonamidoindole or sulfonamidopyrazole. Following cross oxidation, hydrolytic deamidation cleaves the mobile dye with the sulfonamido group attached. Such systems are illustrated by Fleckenstein U.S. Pat. Nos. 3,928,312 and 4,053,312, Fleckenstein et al U.S. Pat. No. 4,076,529, Melzer et al U.K. Pat. No. 1,489,694, Deguchi, German OLS 2,729,820, Koyama et al, German OLS 2,613,005, Vetter et al German OLS 2,505,248, and Kestner et al *Research Disclosure*, Volume 151, November 1976, Item 15157. Also specifically contemplated are otherwise similar systems which employ an immobile, dye releasing (a) hydroquinone, as illustrated by Gompf et al U.S. Pat. No. 3,698,897 and Anderson et al U.S. Pat. No. 3,725,062, (b) para-phenylenediamine, as illustrated by Whitmore et al Canadian Pat. No. 602,607, or (c) quaternary ammonium compound, as illustrated by Becker et al U.S. Pat. No. 3,728,113.

In another specifically contemplated dye image transfer system which is negative working an oxidized electron transfer agent or, specifically, in certain forms, an oxidized para-phenylenediamine reacts with a ballasted phenolic coupler having a dye attached through a sulfonamido linkage. Ring closure to form a phenazine releases mobile dye. Such an imaging approach is illustrated by Bloom et al U.S. Pat. Nos. 3,443,939 and 3,443,940.

In still another negative working system, ballasted sulfonylamidrazones, sulfonylhydrazones or sulfonylcarbonylhydrazides can be reacted with oxidized para-phenylenediamine to release a mobile dye to be transferred, as illustrated by Puschel et al U.S. Pat. Nos. 3,628,952 and 3,844,785. In an additional negative working system, a hydrazide can be reacted with silver halide having a developable latent image site and thereafter decompose to release a mobile, transferable dye, as illustrated by Rogers U.S. Pat. No. 3,245,789, Kohara et al, *Bulletin Chemical Society of Japan*, Volume 43, pages 2433 through 2437, and Lestina et al *Research Disclosure*, Volume 28, December 1974, Item 12832.

Image transfer systems employing negative working image dye providing compounds are also known in which dyes are not initially present, but are formed by reactions occurring in the photographic element or receiver following exposure. For example, a ballasted coupler can react with color developing agent to form a mobile dye, as illustrated by Whitmore et al U.S. Pat. No. 3,227,550, Whitmore U.S. Pat. No. 3,227,552, Bush et al U.S. Pat. No. 3,791,827, and Viro et al U.S. Pat. No. 4,036,643. An immobile compound containing a coupler can react with oxidized para-phenylenediamine to release a mobile coupler which can react with additional oxidized para-phenylenediamine before, during or after release to form a mobile dye, as illustrated by Figueras et al U.S. Pat. No. 3,734,726 and Janssens et al German OLS 2,317,134. In another form, a ballasted amidrazone reacts with an electron transfer agent as a function of silver halide development to release a mobile amidrazone which reacts with a coupler to form a dye at the receiver, as illustrated by Ohyama et al U.S. Pat. No. 3,933,493.

An image to be viewed can be transferred from the image forming layers. A retained image can be formed for viewing as a concurrently formed complement of the transferred image. Positive transferred images and useful negative retained images can be formed with the direct positive silver halide emulsions of this invention when imaging chemistry is negative working. Images retained in and transferred from the image forming layers are illustrated by U.K. Pat. No. 1,456,413, Friedman U.S. Pat. No. 2,543,691, Bloom et al U.S. Pat. No. 3,443,940, Staples U.S. Pat. No. 3,923,510, and Fleckenstein et al U.S. Pat. No. 4,076,529.

Where mobile dyes are transferred to the receiver a mordant is commonly present in a image dye providing layer. Mordants and mordant containing layers are described in the following references which are incorporated by reference: Sprague et al U.S. Pat. No. 2,548,564, Weyerts U.S. Pat. No. 2,548,575, Carroll et al U.S. Pat. No. 2,675,316, Yutzy et al U.S. Pat. No. 2,713,305, Saunders et al U.S. Pat. No. 2,756,149, Reynolds et al U.S. Pat. No. 2,768,078, Gray et al U.S. Pat. No. 2,839,401, Minsk U.S. Pat. Nos. 2,882,156 and 2,945,006, Whitmore et al U.S. Pat. No. 2,940,849, Condax U.S. Pat. No. 2,952,566, Mader et al U.S. Pat. No. 3,016,306, Minsk et al U.S. Pat. Nos. 3,048,487 and 3,184,309, Bush U.S. Pat. No. 3,271,147, Whitmore U.S. Pat. No. 3,271,148, Jones et al U.S. Pat. Nos. 3,282,699, Wolf et al U.S. Pat. No. 3,408,193, Cohen et al U.S. Pat. Nos. 3,488,706, 3,557,066, 3,625,694, 3,709,690, 3,758,445, 3,788,855, 3,898,088, and 3,944,424, Cohen U.S. Pat. No. 3,639,357, Taylor U.S. Pat. No. 3,770,439, Campbell et al U.S. Pat. Nos. 3,958,995 and 4,193,795; and Ponticello et al *Research Disclosure*, Vol. 120, April 1974, Item 12045.

One-step processing can be employed, as illustrated by U.K. Pat. No. 1,471,752, Land U.S. Pat. No. 2,543,181, Rogers U.S. Pat. No. 2,983,606 (pod processing), Land U.S. Pat. No. 3,485,628 (soak image former and laminate to receiver) and Land U.S. Pat. No. 3,907,563 (soak receiver and laminate to image forming element) or multi-step processing can be employed, as illustrated by Yutzy U.S. Pat. No. 2,756,142, Whitmore et al U.S. Pat. No. 3,227,550, and Faul et al U.S. Pat. No. 3,998,637.

Preformed reflective layers can be employed, as illustrated by Whitmore Canadian Pat. No. 674,082, Beavers U.S. Pat. No. 3,445,228, Land U.S. Pat. Nos. 2,543,181, 3,415,644, '645 and '646, and Barr et al U.K. Pat. No. 1,330,524 or processing formed reflective layers can be employed, as illustrated by Land U.S. Pat. Nos. 2,607,685 and 3,647,437, Rogers U.S. Pat. No. 2,983,606, and Buckler U.S. Pat. No. 3,661,585.

Generally, the image transfer film units in accordance with this invention comprise:

(1) a photographic element comprising a support having thereon at least one silver halide emulsion layer containing radiation sensitive internal latent image silver halide grains and a nucleating agent, the emulsion layer preferably having in contact therewith an image dye providing material, (2) an image receiving layer, which can be located on a separate support and superposed or adapted to be superposed on the photographic element or, preferably, can be coated as a layer in the photographic element, (3) an alkaline processing composition, (4) means containing and adapted to release the alkaline processing composition into contact with the emulsion layer, and (5) a silver halide developing agent located in at least one of the photographic element and alkaline processing composition so that the processing composition and developing agent, when brought together, form a silver halide surface developer.

In highly preferred embodiments, the film units of this invention contain a support having thereon a layer containing a blue sensitive emulsion and in contact therewith a yellow image dye providing material, a red sensitive silver halide emulsion and in contact therewith a cyan image dye providing material, and a green sensitive emulsion and in contact therewith a magenta image dye providing material, and preferably all of said image dye providing materials are initially immobile image dye providing materials.

The terms "diffusible" (or "mobile") and "immobile" (or "nondiffusible"), as used herein, refer to compounds which are incorporated in the photographic element and, upon contact with an alkaline processing solution, are substantially diffusible or substantially immobile, respectively, in the hydrophilic colloid layers of a photographic element.

The term "image dye providing material", as used herein, is understood to refer to those compounds which are employed to form dye images in photographic elements. These compounds include dye developers, shifted dyes, color couplers, oxichromic compounds, dye redox releasers, etc, as described above in connection with positive working and negative working image transfer systems.

In one preferred embodiment, the receiver layer is coated on the same support with the photosensitive silver halide emulsion layers, the support is preferably a transparent support, an opaque layer is preferably positioned between the image receiving layer and the photosensitive silver halide layer, and the alkaline processing composition preferably contains an opacifying substance, such as carbon or a pH-indicator dye which is discharged into the film unit between a dimensionally stable support or cover sheet and the photosensitive element.

In certain embodiments, the cover sheet can be superposed or is adapted to be superposed on the photosensitive element. The image receiving layer can be located on the cover sheet so that it becomes an image receiving element. In certain preferred embodiments where the image receiving layer is located in the photosensitive element, a neutralizing layer is located on the cover sheet.

Increases in maximum density can be obtained in color image transfer film units containing internally sulfur and gold sensitized emulsions of the type described by Evans U.S. Pat. No. 3,761,276 and sulfonamidonaphthol redox dye releasing compounds of the type described by Fleckenstein U.K. Pat. No. 1,405,662 by incorporation into the emulsion layers of a variety of chemical addenda generally recognized in the art as antifoggants or development inhibitors, as well as hydrolyzable precursors thereof. Many of these compounds also provide improved stabilization of sensitometric properties of liquid emulsion and of the storage life of the coated emulsion. The effects, shown in film units of the type described in Examples 40 through 42 of U.K. Pat. No. 1,405,662, are in addition to the effect of 5-methylbenzotriazole in the processing composition even when the latter is present in quantities as high as 4 grams per liter. Effective compounds in general are selected from the group consisting of (a) 1,2,3-triazoles, tetrazoles and benzotriazoles having an N—$R^1$ group in the heterocyclic ring, wherein $R^1$ represents hydrogen or an alkali-hydrolyzable group, or (b) heterocyclic mercaptans or thiones and precursors thereof, mostly having one of the formulae (XII) or (XIII):

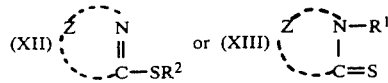

wherein

Z comprises the atoms necessary to complete an azole ring, and $R^2$ represents, in addition to the groups specified above for $R^1$, a metal ion.

The compounds are generally employed at concentrations less than about 300 mg per mole of silver, each compound having an optimum concentration above which development and/or nucleation are inhibited and $D_{max}$ decreases with increasing concentration. Specifically preferred antifoggants and stabilizers, as well as other preferred color image transfer film unit and system features, are more specifically disclosed in *Research Disclosure*, Volume 151, November 1976, Item 15162, the disclosure of which is hereby incorporated by reference.

In a specific preferred form the photographic elements of this invention are intended to produce multicolor images which can be viewed in the elements or in a receiver when the elements form a part of a multicolor image transfer system. For multicolor imaging at least three superimposed color forming layer units are coated on a support. Each of the layer units is comprised of at least one silver halide emulsion layer. At least one of the silver halide emulsion layers, preferably at least one of the silver halide emulsion layers in each color forming layer unit and most preferably each of the silver halide emulsion layers, contain an emulsion according to this invention substantially as described above. The emulsion layers of one of the layer units are primarily responsive to the blue region of the spectrum, the emulsion layers of a second of the layer units are primarily responsive to the green region of the spectrum, and the emulsion layers of a third of the layer units are primarily responsive to the red region of the spectrum. The layer units can be coated in any conventional order. In a preferred layer arrangement the red responsive layer unit is coated nearest the support and is overcoated by the green responsive layer unit, a yellow filter layer and a blue responsive layer unit. When high aspect ratio tabular grain silver halide emulsions are employed, additional preferred layer order arrangements are those disclosed in *Research Disclosure*, Vol. 225, January 1983, Item 22534, here incorporated by reference. The layer units each contain in the emulsion layers or in adjacent hydrophilic colloid layers at least one image dye providing compound. Such compounds can be selected from among those described above. Incorporated dye forming couplers and redox dye releasers constitute exemplary preferred image dye providing compounds. The blue, green and red responsive layer units preferably contain yellow, magenta and cyan image dye providing compounds, respectively.

Negative Working Imaging

The thioamido and alkynyl substituted heterocyclic ammonium salts are capable of increasing the speed of negative working surface latent image forming silver halide emulsions. Surface latent image forming silver halide grains are employed in the overwhelming majority of negative working silver halide emulsions, whereas internal latent image forming silver halide grains, though capable of forming a negative image when developed in an internal developer, are usually employed with surface developers to form direct positive images. The distinction between surface latent image and internal latent image silver halide grains is generally well recognized in the art. Generally some additional ingredient or step is required in preparation to form silver halide grains capable of preferentially forming an internal latent image as compared to a surface latent image.

Although the difference between a negative image produced by a surface latent image emulsion and a positive image produced by an internal latent image emulsion when processed in a surface developer is a qualitative difference which is visually apparent to even the unskilled observer, a number of tests have been devised to distinguish quantitatively surface latent image forming and internal latent image forming emulsions. For example, according to one such test when the sensitivity resulting from surface development (A), described below, is greater than that resulting from internal development (B), described below, the emulsion being previously light exposed for a period of from 1 to 0.01 second, the emulsion is of a type which is "capable of forming a surface latent image" or, more succinctly, it is a surface latent image emulsion. The sensitivity is defined by the following equation:

$$S = 100/Eh$$

in which S represents the sensitivity and Eh represents the quantity of exposure necessary to obtain a mean density—i.e., ½ (D-max+D-min).
Surface Development (A)

The emulsion is processed at 20° C. for 10 minutes in a developer solution of the following composition:

| | |
|---|---|
| N—methyl-p-aminophenol hemisulfate | 2.5 g |
| Ascorbic acid | 10 g |
| Sodium metaborate (with 4 molecules of water) | 35 g |
| Potassium bromide | 1 g |
| Water to bring the total to | 1 liter. |

Internal Development (B)

The emulsion is processed at about 20° C. for 10 minutes in a bleaching solution containing 3 g of potassium ferricyanide per liter and 0.0125 g of phenosafranine per liter and washed with water for 10 minutes and developed at 20° C. for 10 minutes in a developer solution having the following composition:

| | |
|---|---|
| N—methyl-p-aminophenol hemisulfate | 2.5 g |
| Ascorbic acid | 10 g |
| Sodium metaborate (with 4 molecules of water) | 35 g |
| Potassium bromide | 1 g |
| Sodium thiosulfate | 3 g |
| Water to bring the total to | 1 liter. |

The surface latent image forming silver halide emulsions can be comprised of any photographically useful halide or halide mixture (e.g., silver bromide, silver chloride, silver bromoiodide, silver chlorobromide, and silver chlorobromoiodide). For highest attainable speeds, silver bromoiodide emulsions are preferred. The emulsions can include coarse, medium, or fine silver halide grains bounded by {100}, {111}, and/or {110} crystal planes and can be prepared by a variety of techniques—e.g., single-jet, double-jet (including continuous removal techniques), accelerated flow rate and interrupted precipitation techniques, as illustrated by Trivelli and Smith, *The Photographic Journal*, Vol. LXXIX, May, 1939, pages 330–338; T. H. James *The Theory of the Photographic Process*, 4th Ed., Macmillan, 1977, Chapter 3; Terwilliger et al *Research Disclosure*, Vol. 149, September 1976, Item 14987; as well as Nietz et al U.S. Pat. No. 2,222,264; Wilgus German OLS 2,107,118; Lewis U.K. Pat. Nos. 1,335,925, 1,430,465 and 1,469,480; Irie et al U.S. Pat. No. 3,650,757; Morgan U.S. Pat. No. 3,917,485, where pAg cycling is limited to permit retention of surface developability; and Musliner U.S. Pat. No. 3,790,387. The emulsions can be either polydispersed or monodispersed. The same criteria for defining and techniques for achieving monodispersity discussed above in connection with direct positive emulsions are also applicable to these emulsions. Sensitizing compounds, such as compounds of copper, thallium, cadmium, rhodium, tungsten, thorium, iridium and mixtures thereof, can be present during precipitation of the silver halide emulsion, as illustrated by Arnold et al U.S. Pat. No. 1,195,432; Hochstetter U.S. Pat. No. 1,951,933; Overman U.S. Pat. No. 2,628,167; Mueller U.S. Pat. No. 2,950,972; Sidebotham U.S. Pat. No. 3,488,709 and Rosecrants et al U.S. Pat. No. 3,737,313.

The individual reactants can be added to the reaction vessel through surface or sub-surface delivery tubes by gravity feed or by delivery apparatus for maintaining control of the pH and/or pAg of the reaction vessel contents, as illustrated by Culhane et al U.S. Pat. No. 3,821,002, Oliver U.S. Pat. No. 3,031,304 and Claes et al *Photographische Korrespondenz*, Band 102, Number 10, 1967, page 162. In order to obtain rapid distribution of the reactants within the reaction vessel, specially constructed mixing devices can be employed, as illustrated by Audran U.S. Pat. No. 2,996,287, McCrossen et al U.S. Pat. No. 3,342,605, Frame et al U.S. Pat. No. 3,415,650, Porter et al U.S. Pat. No. 3,785,777, Saito et al German OLS 2,556,885 and Sato et al German OLS 2,555,365. An enclosed reaction vessel can be employed to receive and mix reactants upstream of the main reaction vessel, as illustrated by Forster et al U.S. Pat. No. 3,897,935 and Posse et al U.S. Pat. No. 3,790,386.

The grain size distribution of the silver halide emulsions can be controlled by silver halide grain separation techniques or by blending silver halide emulsions of differing grain sizes. The emulsions can include ammoniacal emulsions, as illustrated by *Photographic Chemistry*, Vol. 1, Fountain Press, London, 1958, pages 365–368 and pages 301–304; thiocyanate ripened emulsions, as illustrated by Illingsworth U.S. Pat. No. 3,320,069; thioether ripened emulsions as illustrated by McBride U.S. Pat. No. 3,271,157, Jones U.S. Pat. No. 3,574,628 and Rosecrants et al U.S. Pat. No. 3,737,313 or emulsions containing weak silver halide solvents, such as ammonium salts, as illustrated by Perignon U.S. Pat. No. 3,784,381 and *Research Disclosure*, Vol. 134, June 1975, Item 13452.

Particularly preferred emulsions are high aspect ratio tabular grain emulsions, such as those described in *Research Disclosure*, Item 22534, cited above. Most specifically preferred are high aspect ratio tabular grain silver bromoiodide emulsions also described in Wilgus et al U.S. Pat. No. 4,434,226, Kofron et al U.S. Pat. No. 4,439,520, and Solberg et al U.S. Pat. No. 4,433,048, each filed Sept. 30, 1982, each commonly assigned, and each here incorporated by reference. High aspect ratio tabular grain emulsions are those in which the tabular grains having a diameter of at least 0.6 micron and a thickness of less than 0.5 micron (preferably less than 0.3 micron) have an average aspect ratio of greater than 8:1 (preferably at least 12:1) and account for greater than 50 percent (preferably greater than 70 percent) of the total projected area of the silver halide grains present in the emulsion.

These silver halide emulsions employed to obtain increased photographic imaging speeds as well as other layers of the photographic elements can contain vehicles identical to those described above for direct positive imaging. Conventional proportions of vehicle to silver halide are employed. The emulsions can be washed as described above for direct positive imaging.

It is preferred that the surface latent image forming silver halide emulsions be surface chemically sensitized. Surface chemical sensitization can be undertaken by any convenient conventional technique, typically by one or a combination of middle chalcogen (i.e., sulfur, selenium, and/or tellurium), noble metal (e.g., gold or Group VIII noble metal), or reduction sensitization techniques. Such techniques are illustrated by *Research Disclosure*, Item 17643, cited above, Section III, here incorporated by reference. Preferred high speed surface latent image forming emulsions are gold sensitized emulsions. For example, gold sensitization can be undertaken as taught by Damshroder et al U.S. Pat. No. 2,642,361. Combinations of gold sensitization with middle chalcogen sensitization are specifically contemplated. Generally the highest photographic speeds are achieved with sulfur and gold sensitized silver bromoiodide emulsions, such as taught by Illingsworth U.S. Pat. No. 3,320,069.

Spectral sensitization of the surface latent image forming emulsions can be identical to that described above for direct positive imaging or can embrace any conventional spectral sensitization of surface latent image forming negative working emulsions, such as illustrated by *Research Disclosure*, 17643, cited above, Section IV, here incorporated by reference. Kofron et al, cited above, discloses substantially optimum chemical and spectral sensitizations for high aspect ratio tabular grain silver halide emulsions, particularly silver bromide and silver bromoiodide emulsions.

In their simplest form photographic elements useful in obtaining increased imaging speed need only contain a single layer of an emulsion as described coated on a conventional photographic support. The supports can be identical to those of the direct positive photographic elements. Apart from the requirement of at least one silver halide emulsion layer as described above, the photographic elements can take any convenient conventional form. The photographic elements can produce either silver or dye (including multicolor dye) images. The photographic elements can be similar to the photographic elements described above in connection with direct positive imaging, except that negative working surface latent image forming emulsion is substituted for the internal latent image forming emulsion.

The photographic elements can be used to form either retained or transferred images. When employed to form transferred dye images, the image transfer film units can be similar to those described above in connection with direct positive imaging. However, the high speed negative working emulsion or emulsions are substituted for the direct positive emulsion or emulsions present and therefore positive working transferred dye image providing chemistry will usually be desirably substituted for negative working transferred dye image providing chemistry to provide a positive transferred image. Such modifications are, of course, well within the skill of the art. For image transfer systems useful with the negative working surface latent image forming emulsions, attention is directed to *Research Disclosure*, Item 17643, cited above, Section XXIII, here incorporated by reference. Where high aspect ratio tabular grain emulsions are employed, preferred image transfer systems are those disclosed in *Research Disclosure* Item 22534, cited above.

Antifoggants and stabilizers can be present in the photographic element and/or in the processing solution. Although the antifoggants and stabilizers preferred in connection with direct positive and high contrast imaging can be advantageously employed, the use of conventional antifoggants and stabilizers known to be useful with surface latent image forming emulsions is specifically contemplated. Useful antifoggants and stabilizers are specifically disclosed by *Research Disclosure*, Item 17643, cited above, Section VI, here incorporated by reference.

The thioamido and alkynyl substituted heterocyclic ammmonium salts can be adsorbed to the silver halide grain surfaces in any effective concentration. To avoid elevated minimum density the concentration of the salt should be less than $10^{-2}$ mole per mole of silver. Concentrations of at least $10^{-7}$ mole per mole of silver are specifically contemplated, with a range of from about $10^{-6}$ to $10^{-4}$ mole per mole of silver being preferred.

The increased speed advantages of this invention can be realized employing conventional exposure and processing. Exposure and processing of the photographic elements can be identical to that previously described in connection with direct positive and high contrast imaging, although this is not essential. Generally any conventional manner of exposing and processing surface latent image negative working emulsions can be employed, such as those illustrated by *Research Disclosure,* Item 17643, Sections XVIII, XIX, and XX, here incorporated by reference. The same pH ranges as described above are generally preferred for processing the increased speed photographic elements.

Except as otherwise stated the remaining features of the direct positive and increased speed applications of the invention should be understood to contain features recognized in the art for such photographic applications.

EXAMPLES

The invention can be better appreciated by reference to following specific examples

EXAMPLE 1

Preparation of 6-ethylthiocarbamato-1-propargylquinaldinium trifluoromethanesulfonate (Compound A)

Trifluoromethanesulfonic anhydride (2.5 g, 8.8 mmoles) in 30 ml of carbon tetrachloride was cooled to $-5°$ C. in an ice-salt bath under nitrogen with stirring. A mixture of propargyl alcohol (0.5 g, 8.9 mmoles), pyridine (0.7 g, 8.8 mmoles) and 15 ml of carbon tetrachloride was added dropwise at a rate so as to keep the temperature below $0°$ C. After addition, the ice bath was removed; the mixture was stirred 10 minutes and then filtered through sodium sulfate. Propargyl triflate (hereinafter designated I-1) was the filtrate. The filtrate was added to a solution of 6-isothiocyanatoquinaldine in 50 ml of chloroform and heated to reflux for 3 hours. Fifty ml of ethanol was added and heating was continued for one hour. After cooling the solution was evaporated and the resulting oil was slurried with ether and methylene chloride until a solid formed. The mixture was then placed in the refrigerator overnight. The solid was collected by filtration and recrystallized from ethyl acetate and acetone to give 0.65 g (30% yield) of product, mp 179.5°–180.5° C.

Anal for $C_{17}H_{17}F_3N_2O_4S_2$: Calcd: C, 47.0; H, 3.9; N, 6.4; Found: C, 46.7; H, 3.9; N, 6.3

EXAMPLE 2

Preparation of 6-ethylthiocarbamato 2-methyl-3-propargylbenzothiazolium trifluoromethanesulfonate (Compound B)

6-Isothiocyanato-2-methylbenzothiazole (hereafter referred to as I-2) was prepared as follows: 6-Amino-2-methylbenzothiazole (4.25 g, 25.9 mmoles) was dissolved in dry acetonitrile (50 ml) and cooled with stirring in an ice bath under nitrogen. Thiocarbonyldiimidazole (5.34 g, 30.0 mmoles) was added in portions as a solid over a period of 15 minutes. After stirring for 30 minutes the ice bath was removed. After another 30 minutes of stirring, the mixture was cooled in an ice bath to yield a solid which was collected by filtration and dried; yield 87%, m.p. 118°–120° C.

Anal for $C_9H_6N_2S_2$: Calcd: C, 52.4; H, 2.9; N, 13.6; Found: C, 52.3; H, 2.5; N, 13.4

Trifluoromethanesulfonic anhydride (2.5 g, 8.8 mmoles) in 30 ml of carbon tetrachloride was cooled to $-5°$ C. in an ice-salt bath under nitrogen with stirring. A mixture of propargyl alcohol (0.5 g, 8.9 mmoles), pyridine (0.7 g, 8.8 mmoles) and 15 ml of carbon tetrachloride was added dropwise at a rate so as to keep the temperature below $0°$ C. After addition the ice bath was removed; the mixture was stirred 10 minutes and then filtered through sodium sulfate. The filtrate was added to a solution of I-2 in 50 ml of chloroform and heated to reflux for three hours. Fifty ml of ethanol was added and heating was continued for 1½ hours. After cooling the solution was evaporated and slurried with ether and a small amount of methylene chloride until a solid formed. The solid was collected by filtration and recrystallized from ethyl acetate and acetone to give 1.2 g (38% yield) of product mp 208°–209° C.

Anal for $C_{15}H_{15}F_3N_2S_3O_4$: Calcd: C, 40.9; H, 3.4; N, 6.4; Found: C, 40.7; H, 3.4; N, 6.2

EXAMPLE 3

Preparation of 2-methyl-6-(3-phenylthioureido)-3-propargylbenzothiazolium iodide (Compound C)

I-1 (17.8 mmoles theoretical) was added to a solution of I-2 (3.0 g, 14.6 mmoles) in chloroform (50 ml) and refluxed for one hour. An acetonitrile (20 ml) solution of aniline (2.0 g, 25.9 mmoles) was added and the mixture was refluxed for one hour. After evaporation of the solvents the resulting oil was dissolved in methylene chloride (50 ml) and filtered directly into a methylene chloride solution (50 ml) of tetrabutylammonium iodide (3.0 g, 8.1 mmoles). The mixture was cooled overnight to yield a solid which was collected by filtration and recrystallized from acetonitrile/methanol; yield 0.7 g (10%), m.p. 181°–184° C. of Compound C.

Anal for $C_{18}H_{16}IN_3S_2$: Calcd: C, 46.5; H, 3.5; N, 9.0; Found: C, 46.4; H, 3.3; N, 8.9

EXAMPLE 4

Preparation of 6-(3-methyl-3-phenylthioureido)-2-methyl-3-propargylbenzothiazolium perchlorate (Compound D)

A mixture of I-1 (8.8 mmoles) and I-2 (1.5 g, 7.3 mmoles) in chloroform (50 ml) was refluxed for three hours. A solution of N-methylaniline (1.0 g, 9.3 mmoles) and acetonitrile (20 ml) was added and the mixture was refluxed for 20 minutes. After cooling, the solvents were flash evaporated. The crude product was purified by column chromatography with silica gel. Elution with ether removed starting materials and impurities. The column was eluted next with methanol/methylene chloride (10:90) to yield an oil after evaporation of the solvents. The oil was dissolved in hot water and treated with perchloric acid to yield a white solid which was collected by filtration and dried; yield 0.3 g (10%), m.p. 90° C.

Anal for $C_{19}H_{18}ClN_3O_4S_2 \cdot H_2O$: Calcd: C, 48.6; H, 4.2; N, 8.9; Found: C, 48.5; H, 3.9; N, 9.0

EXAMPLE 5

Preparation of 6-(5-mercapto-1-tetrazolo)-2-methyl-3-propargylbenzothiazolium perchlorate (Compound E)

A mixture of I-1 (8.8 mmoles) and I-2 (1.5 g, 7.3 mmoles) in acetonitrile (50 ml) was refluxed for two hours. The solution was cooled to 5° C. in an ice bath; sodium azide (0.6 g, 9.2 mmoles) in water (25 ml) was added and the mixture was stirred for 30 minutes. After flash evaporation of the solvents, the residue was dissolved in warm water. Excess perchloric acid was added and the resulting white solid (250 mg) was collected by filtration and recrystallized from acetone-/ethyl acetate; yield 60 mg (2%), m.p. 131°–132° C.

Anal for $C_{12}H_{10}ClN_5O_4S_2$: Calcd: C, 37.2; H, 2.6; N, 18.0; Found C, 37.4; H, 2.8

EXAMPLE 6

Preparation of
6-(3-phenylthioureido)-1-propargylquinaldinium iodide
(Compound F)

6-Isothiocyanatoquinaldine (hereinafter referred to as I-3) was prepared in the same manner as described for 6-isothiocyanato-2-methylbenzothiazole, i.e., 6-amino-2-methylquinoline was reacted with thiocarbonyl-diimidazole to give I-3.

A mixture of I-1 (8.8 mmoles) and I-3 (1.5 g, 7.5 mmoles) in chloroform (50 ml) was refluxed for 3 hours. Aniline (0.8 g, 9.7 mmoles) in acetonitrile (20 ml) was added to the solution and the mixture was refluxed for 30 minutes. After cooling, the solvent was removed by flash evaporation; the oily residue was dissolved in methylene chloride (50 ml) and filtered directly into a methylene chloride solution (50 ml) of tetrabutylammonium iodide (3.0 g, 8.1 mmoles). The mixture was cooled overnight to give a solid which was collected by filtration and recrystallized from acetonitrile/methanol; yield 0.8 g (24% yield), m.p. 199°–201° C.

Anal for $C_{20}H_{18}IN_3S$: Calcd: C, 52.3; H, 3.9; N, 9.1; Found: C, 52.4; H, 4.1; N, 9.7

EXAMPLE 7

Preparation of
6-(3-methyl-3-phenylthioureido)-1-propargylquinaldinium perchlorate (Compound G)

Example 7 was prepared like Example 6 except that N-methylaniline (1.0 g, 9.3 mmoles) was used in place of aniline. After cooling the refluxed reaction mixture, the solvents were removed by flash evaporation and the oily residue was purified by column chromatography with silica gel. Elution with ether removed the impurities. Elution with methanol/methylene chloride (10:90) removed the product. The solvents were removed by evaporation; the residue was dissolved in a minimum amount of hot water and filtered into an aqueous solution (50 ml) of excess perchloric acid. The precipitate was collected by filtration and dried; yield 0.3 g (8%), m.p. 94°–98° C.

Anal for $C_{21}H_{20}ClN_3O_4S \cdot \frac{1}{2}H_2O$: Calcd: C, 55.4; H, 4.6; N, 9.1; Found: C, 55.2; H, 4.6; N, 9.7

EXAMPLE 8

Preparation of
6-(5-mercapto-1-tetrazolo)-1-propargylquinaldinium perchlorate (Compound H)

Example 8 was prepared like Example 6 except that sodium azide (0.5 g, 7.7 mmoles) was used in place of aniline. After the addition of sodium azide portion-wise as a solid, the reaction mixture was stirred for 30 min. The reaction mixture was treated next with acetic acid (1.0 g, 16.6 mmole). After evaporation of the solvents, the residue was dissolved in hot water, combined with excess perchloric acid, cooled overnight and filtered to give a solid which was recrystallized from acetone/methanol; yield 0.3 g (10%), m.p. 134°–136° C.

Anal for $C_{14}H_{12}ClN_5O_4S$: Calcd: C, 44.0; H, 3.1; Found: C, 43.7; H, 3.0

EXAMPLE 9

Preparation of
5,6-dichloro-2-methyl-1-[4-(3-methyl-3-phenylthioureido)benzyl]-3-propargylbenzimidazolium perchlorate (Compound I)

5,6-Dichloro-1-(4-isothiacyanatobenzyl)-2-methylbenzimidazole (hereinafter referred to as I-4) was prepared in the same manner as I-2. A mixture of I-1 (8.8 mmoles) and I-4 (2.5 g, 7.1 mmoles) in chloroform (50 ml) was refluxed for one hour. N-methylaniline (1.0 g, 9.3 mmoles) was added to the mixture and after refluxing for an additional 1½ hours, the solvents were evaporated off. The residue was dissolved in hot methanol containing perchloric acid (2 ml). Water was added until the hot solution became slightly cloudy. The hot solution was filtered and then cooled to yield a solid. This solid was collected by filtration and dried; yield 0.25 g (6%), m.p. 112°–115° C.

Anal for $C_{26}H_{23}Cl_3N_4O_4S \cdot \frac{1}{2}H_2O$: Calcd: C, 51.7; H, 3.8; N, 9.3; Found: C, 51.6; H, 3.7; N, 9.7

EXAMPLE 10

Preparation of
5,6-dichloro-3-(4-ethylthiocarbamatobenzyl)-2-methyl-1-propargylbenzimidazolium bromide (Compound J)

I-4 (2.35 g, 6.7 mmoles), propargyl bromide (2.8 g, 23.5 mmoles) and butyronitrile (30 ml) were combined and heated for approximately 15 hours at 110° C. The reaction mixture was cooled and filtered to yield a solid which was dried (1.1 g). Ethanol (50 ml) and 0.6 g of this solid were combined and refluxed for approximately 15 hours. After evaporation of the solvent, the residue was recrystallized from ethyl acetate/ethanol; yield 0.13 g (24%), m.p. 192°–193° C.

Anal for $C_{12}H_{20}BrCl_2N_3OS$: Calcd: C, 49.2; H, 3.9; N, 8.2; Found: C, 48.7; H, 4.0; N, 8.2

EXAMPLE 11

A control coating comprising a sulfur sensitized 0.75 μm octahedral silver bromide emulsion was coated on a film support at 4.09 g Ag/m² with an overcoat layer of gelatin (0.65 g/m²). The coating was exposed (2 sec/500 W, 5500° K.) through a graduated density stepwedge and processed (1 min/21.1° C.) in a hydroquinone surface developer. Table II lists the sensitometric results.

The procedure above was repeated, except that the coating contained 0.06 mmole of Compound A/mole Ag. The sensitometric data are shown in Table II.

TABLE II

| Compound | D-max |
|----------|-------|
| None | 0.41 |
| A | 3.65 |

EXAMPLE 12

A 0.75 μm octahedral silver bromide emulsion internally sensitized with sulfur plus gold and surface sensitized with sulfur was coated on a film support at 4.09 g Ag/m² and 5.81 gel/m² with an overcoat layer of 0.65 g gel/m². The coating was exposed (2 seconds at 500 W, 5500° K.) through a graduated density step tablet and processed (30 seconds at 21.2° C.) in a hydroquinone-Phenidone® (1-phenyl-3-pyrazolidone) developer. The sensitometric results for this direct reversal is shown in Table III.

The procedure above was repeated, except that the coatings contained 0.06 mmole Compound A/mole Ag. The results were as follows:

TABLE III

| Compound | Reversal D-min | Reversal D-max |
|----------|----------------|----------------|
| None     | 0.06           | 0.07           |
| A        | 0.19           | 2.20           |

EXAMPLE 13

A coarse-grain sulfur and gold sensitized silver bromoiodide x-ray emulsion was combined with 2-methyl-2,4-pentanediol, gelatin, saponin, 4-hydroxy-6-methyl-1,3,3a,7-tetraazaindene, anhydro-5-chloro-9-ethyl-5'-phenyl-3'-(3-sulfobutyl)-3-(3-sulfopropyl)oxacarbocyanine hydroxide, sodium salt and coated on a film support at 4.3 g Ag/m$^2$ and 4.8 g gel/m$^2$. The dried coating was exposed for 1/50 second to simulated blue screen light and processed for 3 minutes in an hydroquinone-Elon® (N-methyl-p-aminophenol sulfate) surface developer at 20° C. The sensitometric results are listed in Table IV.

The procedure above was repeated, except that the coating also contained 0.38 μmole Compound A/mole Ag. The results are in Table IV.

TABLE IV

| Compound | Relative Speed | D-min |
|----------|----------------|-------|
| None     | 110            | 0.10  |
| A        | 115            | 0.13  |

EXAMPLE 14

Example 13 was repeated, but with the spectral sensitizing dye omitted. A similar speed increase was observed as in Example 13.

EXAMPLE 15

Compound A ($1.8 \times 10^{-4}$ mole/mole Ag) was added to a 0.40 μm cubic AgBr core/shell emulsion (sulfur plus gold sensitized core and sulfur sensitized shell) which was spectrally sensitized to the blue region with anhydro-1,3'-bis(3-sulfopropyl)naphtho[1,2-d]-thiazolothiacyanine hydroxide, sodium salt (200 mg/mole Ag). The emulsion was coated at 2.04 g Ag/m$^2$ and 4.09 g gel/m$^2$ on a film support. The dried coating was exposed ($10^{-5}$ seconds EG&G exposure with a P-11 filter and 0.3 neutral density filter) and processed for 25 seconds/43.3° C. in a roller transport processor containing Kodak Developer D-19® (an N-methyl-p-aminophenol hemisulfate-hydroquinone developer) and 5-methylbenzotriazole (0.2 g/l). Another set of this coating was stored for seven days at 48.9° C./50% RH, exposed and processed in the same manner. The sensitometric data are in Table V below.

Compound K was added to the same emulsion at two levels, $3.78 \times 10^{-4}$ mole/mole Ag and $7.56 \times 10^{-4}$ mole/mole Ag, and coated in the same manner. The coatings were tested in the same manner as described above for Compound A. The sensitometric data are in Table V below.

Maximum density did not vary on incubation when Compound A was employed; on the contrary, however, loss in Dmax was observed with Compound K. When Compound K was used at a higher concentration ($7.56 \times 10^{-4}$ mole/mole Ag) to achieve a Dmax (2.1) equal to that which was observed when Compound A was present, the incubated coatings fogged.

EXAMPLE 16

Similar results were observed when Example 15 was repeated substituting Compound D for Compound A. The sensitometric data are in Table V below.

TABLE V

| Compound | Mole/Mole Ag | *Rel. Speed | γ | D min | D max |
|----------|--------------|-------------|---|-------|-------|
| Fresh    |              |             |   |       |       |
| A | $1.80 \times 10^{-4}$ | 100 | 3.6 | 0.04 | 2.1 |
| D | $1.80 \times 10^{-4}$ | 105 | 2.5 | 0.05 | 1.8 |
| K | $3.78 \times 10^{-4}$ | 174 | 2.8 | 0.04 | 1.9 |
| K | $7.56 \times 10^{-4}$ | 95  | 3.1 | 0.04 | 2.1 |
| One Week 48.9° C./50% RH | | | | | |
| A | $1.80 \times 10^{-4}$ | 85  | 3.0 | 0.09 | 2.1  |
| D | $1.80 \times 10^{-4}$ | 87  | 2.3 | 0.09 | 1.75 |
| K | $3.78 \times 10^{-4}$ | 205 | 1.5 | 0.06 | 1.3  |
| K | $7.56 \times 10^{-4}$ | —   | —   | 1.4  | 1.95 |

*Measured at 0.10 above D min

EXAMPLE 17

A series of photographic single color image transfer elements were prepared having the following layers coated on a clear polyester support. The coatings differed only in the type and level of nucleating agent in the emulsion layer. All values in parentheses are in g/m$^2$ unless indicated otherwise.

1. Gelatin (1.29), magenta dye-releaser D (0.48) and sodium 5-octadecylhydroquinone-2-sulfonate (5 g/mole Ag). Dye releaser D is Compound XVI in Fernandez U.S. Pat. No. 4,135,929.
2. A green sensitive internal image silver bromide (0.48 Ag) gelatin (1.29) emulsion including sodium 5-octadecylhydroquinone-2-sulfonate (6 g/mole Ag) and Compound A ($1.62 \times 10^{-4}$ mole/mole Ag).
3. An overcoat layer of gelatin (1.29), didodecyl hydroquinone (0.22), developing agent Compound 44 of U.S. Pat. No. 4,358,525 (0.52) and bis(vinylsulfonyl)methane hardener (1%).

The elements were exposed (500 W, 3200° K.+W99 filter) for five seconds through a multicolor graduated density test object and soaked for 15 seconds at 28° C. in an activator solution containing the following components:

| Components | g/l |
|------------|-----|
| 5-Methylbenzotriazole | 3.0 |
| 11-Aminoundecanoic acid | 2.0 |
| Potassium bromide | 2.0 |
| Made up to 1 liter with 0.6 N potassium hydroxide | |

After soaking, the element was laminated to a dye image receiver (structure given below) for 4 minutes at ~21.0° C. and then peeled apart. The receiver was washed with distilled water, air dried, and read on a densitometer.

The dye image receiver of the following structure was prepared as follows; coverages are in g/m$^2$:

4. Gelatin overcoat layer (0.65) containing zinc sulfate (90.04)
3. Interlayer of 2-(2-hydroxy-3,5-di-t-amylphenyl)benzotriazole (0.54) in gelatin (0.86)

2. Image receiving layer: Mordant:poly(styrene-co-1-vinylimidazole-co-3-(2-hydroxyethyl)-2-vinylimidazolium chloride), weight ratio 50:40:10 (2.4), sorbitol (0.54), gelatin (3.0)
1. Gelatin (0.81), plus formaldehyde equal to 1.25% of the total gelatin weight Coated on opaque paper stock.

Listed below in Table VI are data which compare the relative nucleating activity of other compounds with nucleating agent Compound A. The activity rating value is based upon the concentration of nucleating agent that is required to give an equivalent H and D curve; i.e., similar D-max, contrast, speed, and D-min as nucleating agent Compound A.

With Compound A assigned an activity rating of 1.0, a nucleating agent with a rating of 2.0 is twice as active, i.e., only one-half the concentration of the nucleating agent on a molar basis is required to give the same relative curve shape as Compound A.

TABLE VI

| Compound | Molar Reactivity Relative to A |
|---|---|
| A | 1.00 |
| L | 0.63 |
| M | 0.31 |

The invention has been described in detail with particular reference to preferred embodiments thereof, but it will be understood that variations and modifications can be effected within the spirit and scope of the invention.

What is claimed is:

1. A radiation sensitive silver halide emulsion comprised of a dispersing medium, silver halide grains, and, adsorbed to the surface of the silver halide grains, a heterocyclic quaternary ammonium salt of the formula:

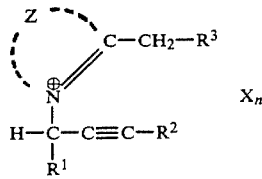

wherein
Z represents the atoms completing a heterocyclic quaternary ammonium nucleus comprised of an azolium or azinium ring;
$R^1$ is hydrogen or methyl;
$R^2$ is hydrogen or an alkyl substituent of from 1 to 8 carbon atoms;
$R^3$ is hydrogen or a substituent having a Hammett sigma value derived electron withdrawing characteristic more positive than $-0.2$;
X is a charge balancing counter ion; and
n is 0 or 1; and
Z or $R^3$ includes a thioamido adsorption promoting moiety.

2. A radiation sensitive silver halide emulsion according to claim 1 wherein said silver halide grains are capable of forming a surface latent image and said heterocyclic quaternary ammonium salt is present in a speed increasing amount.

3. A radiation sensitive silver halide emulsion according to claim 1 wherein said silver halide grains are capable of forming an internal latent image and said heterocyclic quaternary ammonium salt is present in an amount sufficient to promote development of unexposed silver halide grains in a surface developer.

4. A radiation sensitive silver halide emulsion according to claim 1 wherein said heterocyclic quaternary ammonium salt is present in a concentration of up to $10^{-2}$ mole per silver mole.

5. A radiation sensitive silver halide emulsion according to claim 1 wherein at least one of $R^1$ and $R^2$ is hydrogen.

6. A radiation sensitive silver halide emulsion according to claim 5 wherein each of $R^1$ and $R^2$ is hydrogen.

7. A radiation sensitive silver halide emulsion according to claim 1 wherein Z represents the atoms completing a nucleus chosen from the class consisting of thiazolinium, thiazolium, benzothiazolium, naphthothiazolium, selenazolium, benzoselenazolium, naphthoselenazolium, benzimidazolium, tetrazolium, pyridinium, quinolinium, and indolenium nuclei.

8. A radiation sensitive silver halide emulsion according to claim 1 wherein said thioamido adsorption promoting moiety is chosen from among oxythioamido, dithioamido, and thioureido adsorption promoting moieties.

9. A radiation sensitive silver halide emulsion according to claim 8 wherein said thioamido adsorption promoting moiety is linked through Z.

10. A radiation sensitive silver halide emulsion according to claim 9 wherein said thioamido adsorption promoting moiety is a direct ring substituent of Z.

11. A radiation sensitive silver halide emulsion according to claim 10 wherein said thioamido adsorption promoting moiety is of the formula:

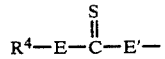

wherein
one of E and E' represents $-N(R^5)-$ and the other represents $-O-$, $-S-$, or $-N(R^6)-$;
$R^4$ represents hydrogen, aliphatic residue, an aromatic residue, or together with E or E' completes a heterocyclic ring;
$R^5$ or $R^6$ in the E position represents hydrogen, an aliphatic residue, or an aromatic residue; and
$R^5$ or $R^6$ in the E' position represents hydrogen or a benzyl substituent;
provided that at least one of $R^4$, $R^5$, and $R^6$ must be hydrogen when each is present.

12. A photographic element comprised of a support and at least one layer of a silver halide emulsion according to claim 1.

13. A negative working photographic element comprised of a support and one or more silver halide emulsion layers, at least one of said emulsion layers being comprised of a silver halide emulsion according to claim 2.

14. A negative working photographic element according to claim 13 additionally including dye image providing means.

15. In a negative working photographic element of intermediate or lower contrast comprised of a support and one or more silver halide emulsion layers, at least one of said emulsion layers being comprised of a dispersing medium and gold sensitized surface latent image forming silver halide grains, the improvement comprising, adsorbed to the surface of said gold sensitized silver halide grains, a heterocyclic ammonium salt of the formula:

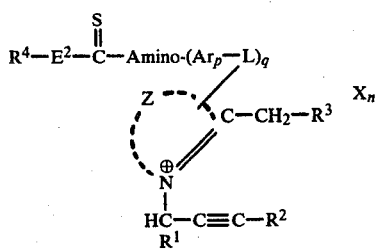

wherein
- Z represents the atoms completing a heterocyclic quaternary ammonium nucleus comprised of an azolium or azinium ring;
- $R^1$ is hydrogen or methyl;
- $R^2$ is hydrogen or an alkyl substituent of from 1 to 8 carbon atoms;
- $R^3$ is hydrogen or a substituent having a Hammett sigma value derived electron withdrawing characteristic more positive than $-0.2$;
- $R^4$ is hydrogen or an alkyl or aryl substituent of from 1 to 18 carbon atoms;
- $E^2$ is —O— or —Amino—;
- Amino is a primary or secondary amino moiety;
- Ar is an arylene group;
- L is a divalent aliphatic linking group;
- X is a charge balancing counter ion; and
- n, p, and q are independently 0 or 1.

16. A negative working photographic element according to claim 15 wherein said heterocyclic ammmonium salt is present in a concentration of from $10^{-7}$ to $10^{-2}$ mole per mole of silver.

17. A negative working photographic element according to claim 16 wherein said heterocyclic ammonium salt is present in a concentration of from $10^{-6}$ to $10^{-4}$ mole per mole of silver.

18. A negative working photographic element according to claim 15 wherein $R^4$ is an alkyl or a phenyl substituent.

19. A negative working photographic element according to claim 15 wherein p is 0 and q is 1.

20. A negative working photographic element according to claim 15 wherein p is 1 and Amino is —N(R$^5$)—, where $R^5$ is hydrogen or a benzyl substituent.

21. A direct positive photographic element comprised of a support and one or more silver halide emulsion layers, at least one of said emulsion layers being comprised of a silver halide emulsion according to claim 3.

22. In a direct positive photographic element comprised of a support and one or more silver halide emulsion layers comprised of a dispersing medium, internal latent image forming silver halide grains, and a heterocyclic quaternary ammonium salt nucleating agent, the improvement comprising, adsorbed to the surface of said silver halide grains, a heterocyclic quaternary ammmonium salt nucleating agent is of the formula:

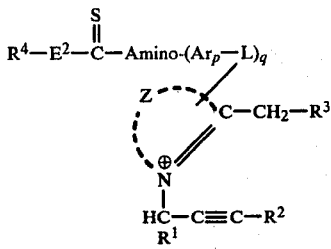

wherein
- Z represents the atoms completing a heterocyclic quaternary ammonium nucleus comprised of azolium or azinium ring;
- $R^1$ is hydrogen or methyl;
- $R^2$ is hydrogen or an alkyl substituent of from 1 to 8 carbon atoms;
- $R^3$ is hydrogen or a substituent having a Hammett sigma value derived electron withdrawing characteristic more positive than $-0.2$;
- $R^4$ is hydrogen or an alkyl or aryl substituent of from 1 to 18 carbon atoms;
- $E^2$ is —O— or —Amino—;
- Amino is a primary or secondary amino moiety;
- Ar is an arylene group;
- L is a divalent aliphatic linking group;
- X is a charge balancing counter ion; and
- n, p, and q are independently 0 or 1.

23. A direct positive photographic element according to claim 22 wherein said heterocyclic quaternary ammonium salt is present in a concentration of from $10^{-5}$ to $10^{-3}$ mole per mole of silver.

24. A direct positive photographic element according to claim 22 wherein $R^4$ is an alkyl or a phenyl substituent.

25. A direct positive photographic element according to claim 22 wherein p is 0 and q is 1.

26. A direct positive photographic element according to claim 22 wherein p is 1 and Amino is —N(R$^5$)—, where $R^5$ is hydrogen or a benzyl substituent.

27. A direct positive photographic element according to claim 22 particularly adapted for producing a viewable silver image.

28. A direct positive photographic element according to claim 22 including a dye image forming material.

29. In a photographic image transfer film unit comprising
- a support,
- at least one emulsion layer located on said support containing a dispersing medium, radiation sensitive internal latent image forming silver halide grains, and a heterocyclic quaternary ammonium salt nucleating agent,
- a dye image providing material present in said emulsion layer or a layer adjacent thereto, and
- a receiving layer for providing a viewable transferred dye image following imagewise exposure and processing of said emulsion layer, the improvement comprising, said heterocyclic quaternary ammonium salt being adsorbed to said silver halide grain surfaces and being of the formula:

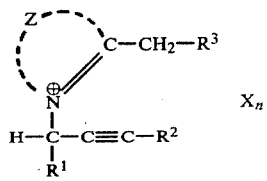

wherein

Z represents the atoms completing a heterocyclic quaternary ammonium nucleus comprised of an azolium or azinium ring;

$R^1$ is hydrogen or methyl;

$R^2$ is hydrogen or an alkyl substituent of from 1 to 8 carbon atoms;

$R^3$ is hydrogen or a substituent having a Hammett sigma value derived electron withdrawing characteristic more positive than −0.2;

X is a charge balancing counter ion; and n is 0 or 1; and

Z or $R^3$ includes a thioamido adsorption promoting moiety.

30. An image transfer film unit according to claim 29 wherein said heterocyclic quaternary ammonium salt is present in a concentration of from $10^{-5}$ to $10^{-3}$ mole per mole of silver.

31. An image transfer film unit according to claim 29 wherein said heterocyclic quaternary ammonium salt is of the formula:

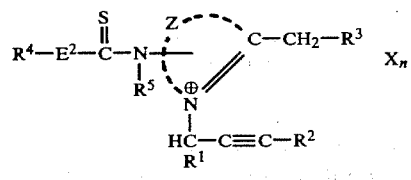

wherein

Z represents the atoms completing a heterocyclic quaternary ammonium nucleus chosen from the group consisting of thiazolinium, thiazolium, benzothiazolium, naphthothiazolium, selenazolium, benzoselenazolium, naphthoselenazolium, benzimidazolium, tetrazolium, pyridinium, quinolinium, and indolenium nuclei;

$R^1$ is hydrogen or methyl;

$R^2$ is hydrogen or methyl;

$R^3$ is hydrogen or a substituent having a Hammett sigma value derived electron withdrawing characteristic more positive than −0.2;

$R^4$ is an alkyl or an aryl substituent;

$R^5$ is hydrogen or a benzyl substituent;

X is a charge balancing counter ion;

n is 0 or 1;

$E^2$ is oxygen or $-N(R^6)-$; and $R^6$ is hydrogen or an aliphatic or aromatic residue of from 1 to 18 carbon atoms.

32. An image transfer film unit according to claim 31 wherein at least one of $R^1$ and $R^2$ are hydrogen.

33. A direct positive photographic element according to claim 22 in which Z completes a quinolinium nucleus.

34. A direct positive photographic element according to claim 22 in which Z completes a benzothiazolium nucleus.

35. A direct positive photographic element according to claim 22 in which Z completes a benzimidazolium nucleus.

36. A direct positive photographic element according to claim 22 in which said quaternary ammonium salt is chosen from the group consisting of (a) a 6-ethylthiocarbamato-1-propargylquinaldinium salt, (b) a 6-ethylthiocarbamato-2-methyl-1-propargylbenzothiazolium salt, (c) a 2-methyl-6-(3-phenylthioureido)-3-propargylbenzothiazolium salt, (d) a 6-(3-methyl-3-phenylthioureido)-2-methyl-3-propargylbenzothiazolium salt, (e) a 6-(5-mercapto-1-tetrazolo)-2-methyl-3-propargylbnezothiazolium salt, (f) a 6-(3-phenylthioureido)-1-propargylquinaldinium salt, (g) a 6-methyl-3-phenylthioureido)-1-propargylquinaldinium salt, (h) a 6-(5-mercapto-1-tetrazolo)-1-propargylquinaldinium salt, (i) a 5,6-dichloro-2-methyl-1-[4-(3-methyl-3-phenylthioureido)benzyl]3-propargylbenzimidazololium salt, and (j) a 5,6-dichloro-3-(4-ethylthiocarbamatobenzyl)-2-methyl-1-propargylbenzimidazolium salt.

* * * * *

UNITED STATES PATENT AND TRADEMARK OFFICE
CERTIFICATE OF CORRECTION

PATENT NO. : 4,471,044
DATED : September 11, 1984
INVENTOR(S) : Parton et al

It is certified that error appears in the above-identified patent and that said Letters Patent is hereby corrected as shown below:

Column 6, line 14, after "5-ethyl-$\beta$-naphthothiazolium", insert -- nuclei --. Column 17, line 51, delete "as vehicles". Column 21, line 39, delete ", benzoselenazole" and substitute therefor -- or benzoselenazole, either of --. Column 32, line 8, before "17643", insert -- Item --.

Column 36, line 66, after "5.81", insert -- g --. Column 38, line 66, delete "(90.04)" and substitute therefor -- (0.04) --.

Signed and Sealed this

Fifth Day of August 1986

[SEAL]

Attest:

DONALD J. QUIGG

Attesting Officer

Commissioner of Patents and Trademarks